United States Patent [19]
Schmitz

[11] Patent Number: 5,968,031
[45] Date of Patent: *Oct. 19, 1999

[54] DISPOSABLE ABSORBENT ARTICLE HAVING AN EXTENSIBLE LANDING MEMBER FORMED FROM AN EXTENSION OF THE INNER LAYER

[75] Inventor: Christoph Johann Schmitz, Euskirchen-Stotzheim, Germany

[73] Assignee: The Procter & Gamble Company, Cincinnati, Ohio

[ * ] Notice: This patent is subject to a terminal disclaimer.

[21] Appl. No.: 09/204,577

[22] Filed: Dec. 3, 1998

Related U.S. Application Data

[62] Division of application No. 08/894,293, Aug. 15, 1997, Pat. No. 5,897,547.

[30] Foreign Application Priority Data

Feb. 16, 1995 [EP] European Pat. Off. ............... 95102144

[51] Int. Cl.[6] ...................................................... A61F 13/15
[52] U.S. Cl. ............................................ 604/391; 604/386
[58] Field of Search ................................... 604/385.1, 386, 604/391

[56] References Cited

U.S. PATENT DOCUMENTS

| | | | |
|---|---|---|---|
| 5,032,122 | 7/1991 | Noel et al. | 604/391 |
| 5,057,097 | 10/1991 | Gesp | 604/390 |
| 5,112,326 | 5/1992 | Quadrini | 604/391 |
| 5,615,460 | 4/1997 | Weirich et al. | 604/391 |
| 5,735,840 | 4/1998 | Kline et al. | 604/391 |
| 5,763,041 | 6/1998 | Leak et al. | 604/391 |
| 5,795,350 | 8/1998 | Schmitz | 604/391 |
| 5,797,896 | 8/1998 | Schmitz | 604/391 |
| 5,853,404 | 12/1998 | Schmitz | 604/391 |

*Primary Examiner*—Mark O. Polutta
*Attorney, Agent, or Firm*—David M. Weirich; Steven W. Miller; Jacobus C. Rasser

[57] ABSTRACT

An absorbent article comprising: a backsheet having a user-facing side, a garment-facing side, two longitudinal sides, a first transverse edge, a first waist region located along the first transverse edge, a second transverse edge, and a second waist region located along the second transverse edge. The absorbent article includes an inner layer covering at least a part of the user-facing side of the backsheet, an absorbent core located adjacent the user facing side of the backsheet, and a mechanical fastening system. The fastening system comprises at least one hook-type fastening member located in the second waist region and extending transversely beyond one longitudinal side, and an extensible landing member located in the first waist region for mechanically engaging with the hook-type fastening member. The landing member is formed from an extension of the inner layer which extends beyond the front transverse edge of the backsheet.

13 Claims, 19 Drawing Sheets

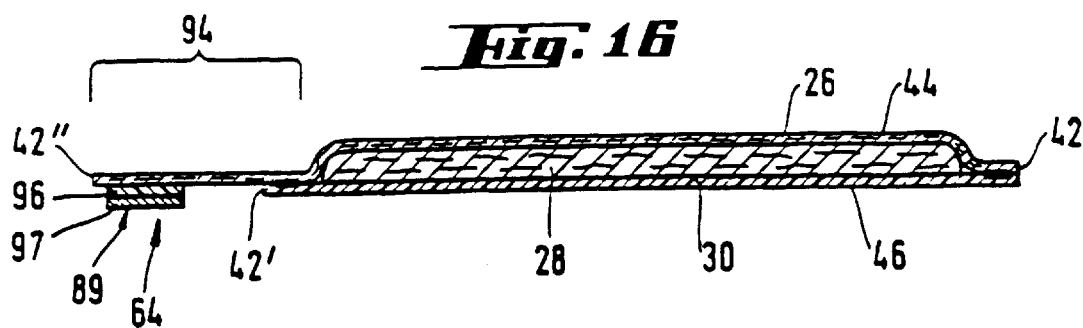
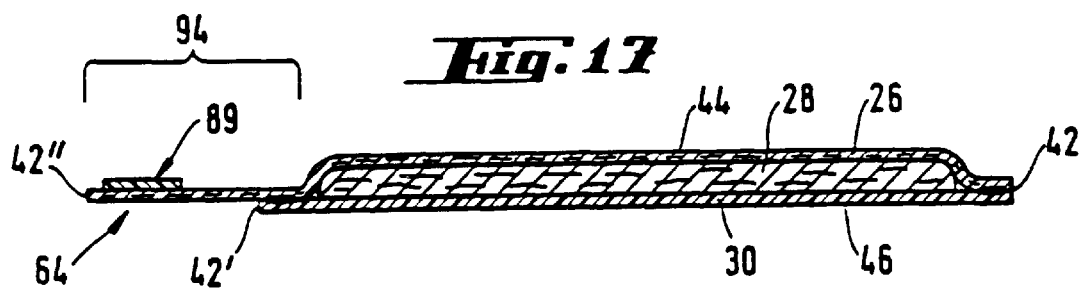
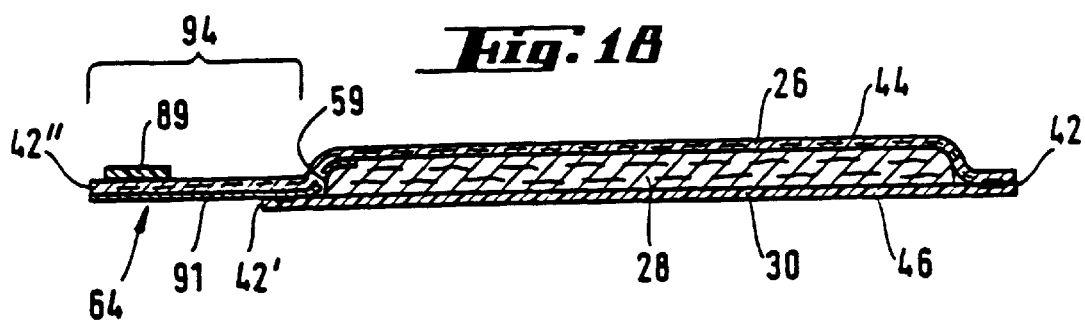
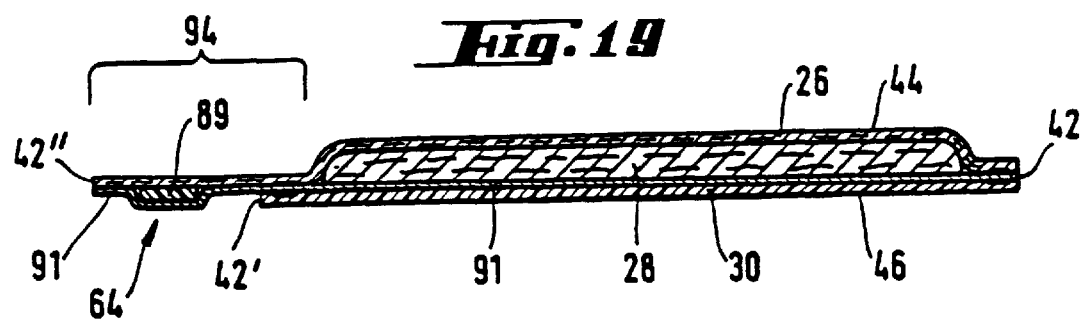

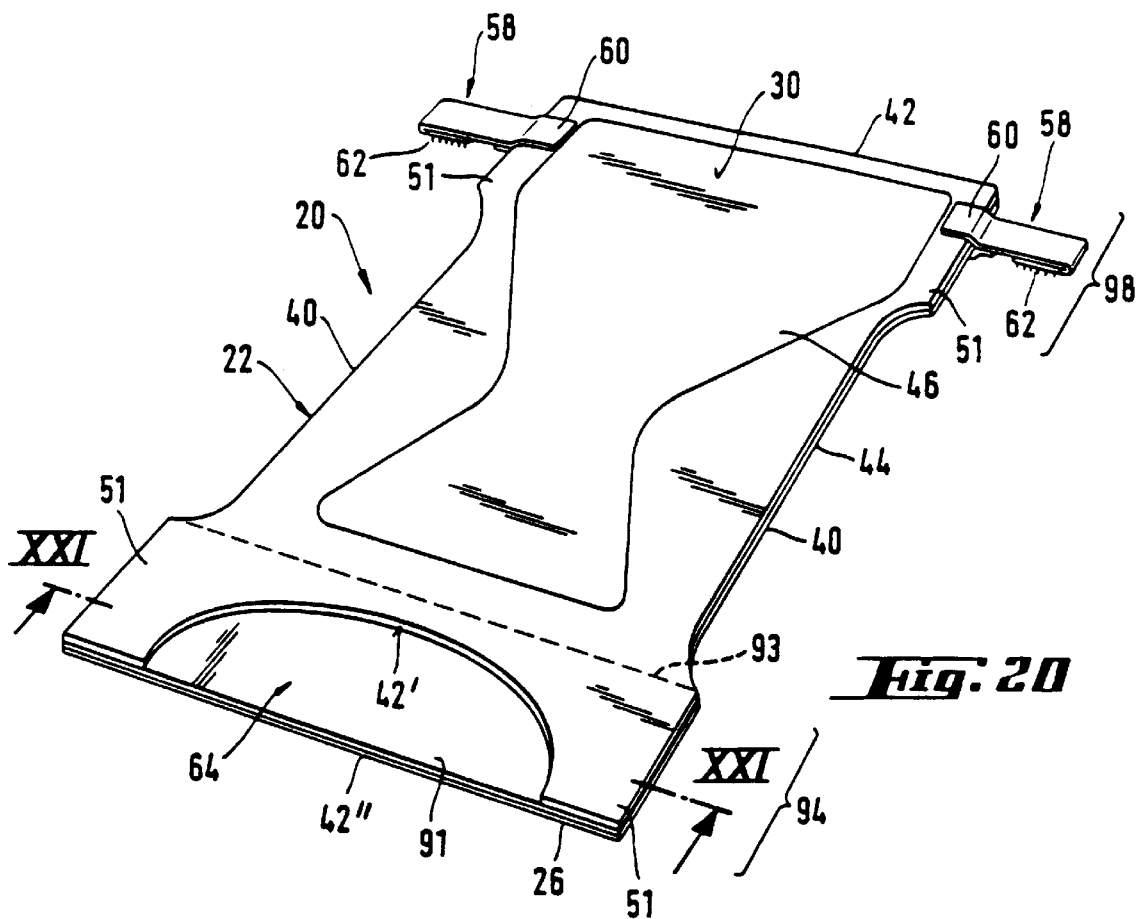
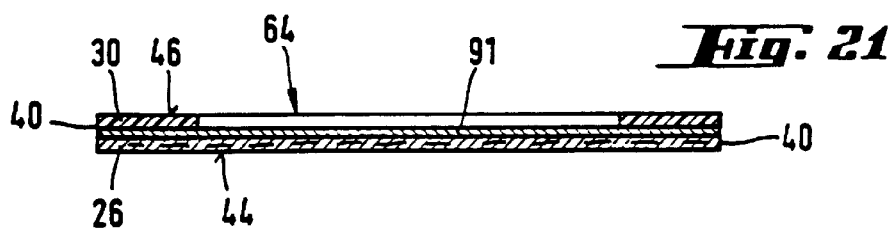
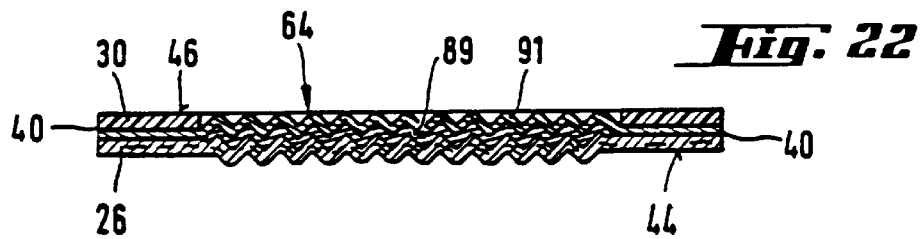

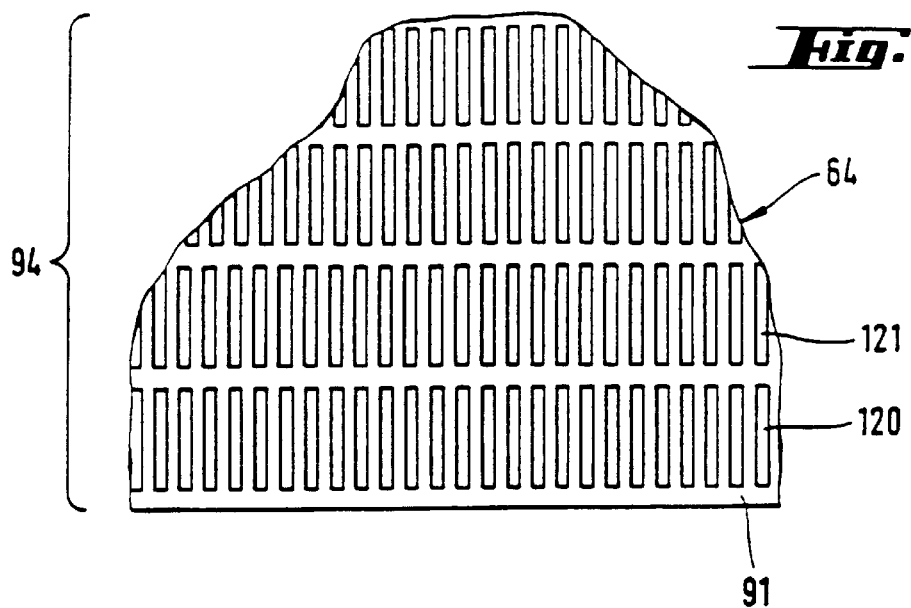
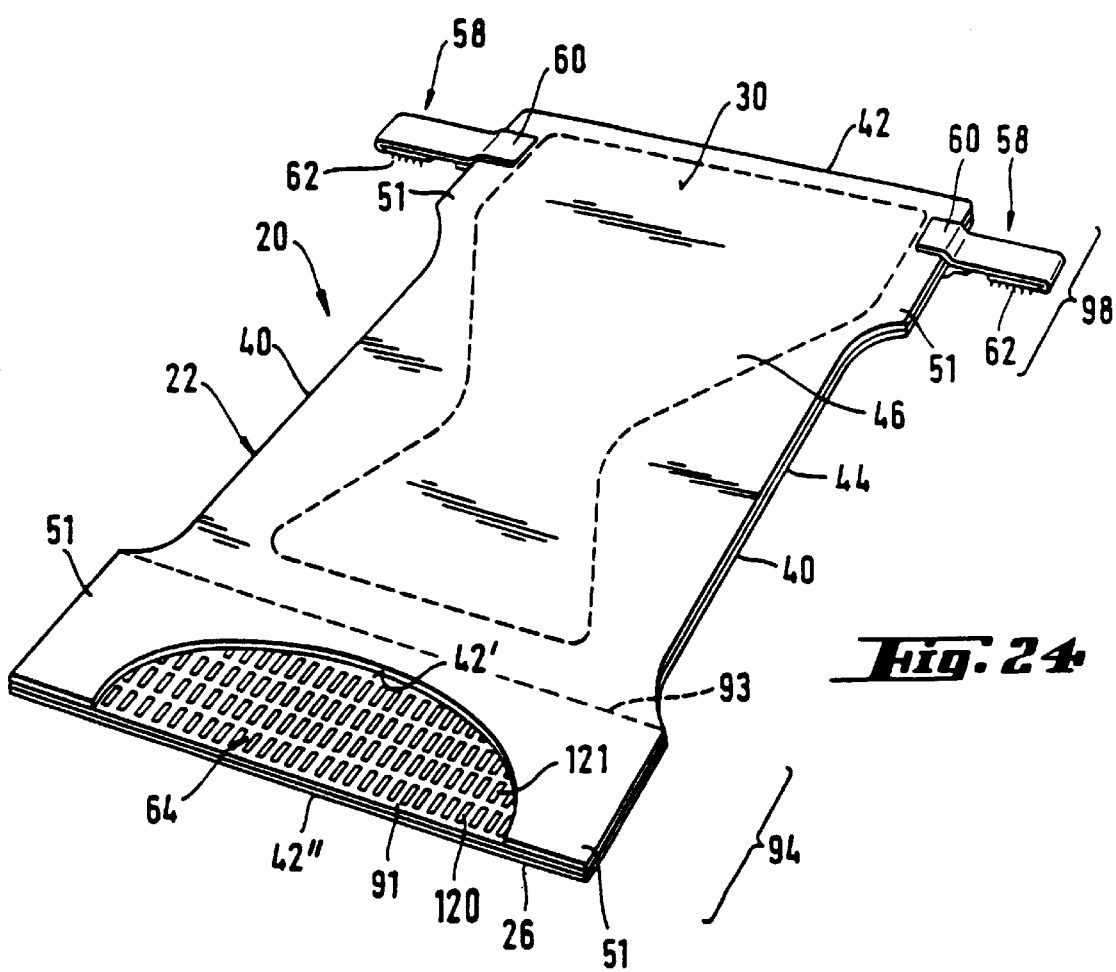

DISPOSABLE ABSORBENT ARTICLE HAVING AN EXTENSIBLE LANDING MEMBER FORMED FROM AN EXTENSION OF THE INNER LAYER

This is a division of application Ser. No. 08/894,293, filed on Aug. 15, 1997 now U.S. Pat. No. 5,897,547.

FIELD OF THE INVENTION

The invention relates to disposable absorbent articles comprising a mechanical fastening system.

Such disposable absorbent articles are know from EP-A-0 321 234.

Known mechanical fastening systems for use in disposable absorbent articles comprise tape tabs comprising a hook-type fastening element in the back waist region wherein the hooks mechanically engage with a landing member. The landing member is a loop-type material located in the front waist region on the garment-facing side of the article which entangles with the hooks of the tape tabs to form a closure having resistance against peel forces and shear forces.

The loop-type materials used for the landing members of the known mechanical fastening systems are relatively expensive materials.

Furthermore, the known loop-type materials are attached to the garment-facing side of the backsheet and form an extra layer that increases the bulk of the absorbent articles upon compression-packaging of these articles in a compressed array.

By attaching relatively small sized patches of loop-type material to the backsheet, the complexity of the production process for making an absorbent article is increased. The addition of larger patches, or strips of loop-type material to the garment-facing side of the backsheet, may cause the elastic expansion of the materials in the front waist region of the absorbent article to be impaired.

Finally, when an elasticated front waist region is provided in an absorbent article, the material of the backsheet in this region will comprise a number of gathers or surface irregularities, caused by the contraction of the elastic element in the front waist region. Patches of loop-type material cannot properly be attached to such irregularly shaped surfaces.

It is therefore an object of the present invention to provide an absorbent article having a mechanical fastening system which allows good conformability of the front waist region to the movements of the user and which allows dynamic and self-adjusting fit of the front waist region.

It is another object of the present invention to provide an absorbent article having a mechanical fastening system which can easily be applied in the region of an elasticated front waist region.

It is again another object of the invention to provide a mechanical fastening system which is of relatively simple construction and which is cost-effective.

It is a further object of the invention to provide an absorbent article comprising a mechanical fastening system which is of low bulk when packed in a compressed array.

SUMMARY OF THE INVENTION

An absorbent article according to the invention comprises a garment-facing backsheet having two longitudinal sides, a front transverse edge, and a back transverse edge. The article has a mechanical fastening system for attaching the article to a wearer, comprising at least two hook-type fastening members located in the region of the back transverse edge and extending transversely beyond each longitudinal side. A loop-type landing member is located in the region of the front transverse edge for mechanically engaging with the hook-type fastening members, wherein the landing member is elastically extensible by at least 5% in the direction of the front transverse edge.

The landing member may be made of an elastic loop-type material, such as for instance an elastic non-woven material. The elastic loop-type material in such an embodiment forms the front waist elastic element of the front waist region while simultaneously allowing the hook-type material to fasten the absorbent article on the wearer. Alternatively, the landing member comprises a non-elastic loop-type material, which is laminated to an elastic film.

The above landing members may be attached to the garment-facing side of the front waist region of the backsheet in a pre-stretched manner, such that the contraction of the landing member contracts the front waist region in a number of gathers. Alternatively, the landing member may be attached to the backsheet in a relaxed state, and may be subsequently mechanically deformed or pre-strained to impart extensibility to the landing member. Mechanical deformation may for instance be imparted by passing the landing member between a pair of intermeshing, grooved rolls, such as described in U.S. Pat. No. 5,196,000 and U.S. Pat. No. 5,236,430.

The landing member may also comprise a patch or strip of loop-type material that is superimposed on a front waist elastic element applied to the topsheet or the backsheet of the absorbent article in the front waist region, such that the loop-type material is contracted by the waist elastic element in gathers. The contraction of the front waist elastic element will cause the loops, or fibers, on the surface of the landing member to project outwardly, and thereby improves the fastening characteristics thereof In one embodiment of an absorbent article according to the invention, an inner layer is located on the garment-facing side of the backsheet. The landing member comprises at least one cut-out section extending through the backsheet and exposing the underlying inner layer. The part of the underlying layer located below the at least one cut-out section, is adapted to mechanically engage with the hook-type fastening members and forms a part of the landing member.

By cutting an aperture through the backsheet material, the inner layer below the backsheet is exposed through the aperture. The inner layer, which for instance comprises a fibrous non-woven layer, may be the topsheet which covers the absorbent core or may be a layer located between the topsheet and the backsheet. Alternatively, the inner layer may be a layer which is located below the absorbent core or may be a high wet-strength tissue which envelopes the core. By selecting the hook-type fastening members to match the non-woven material that is regularly employed as an inner layer, the hooks can mechanically engage with these layers to fasten the absorbent article around a wearer.

In another embodiment of an absorbent article according to the invention, the landing member defines a landing zone for receiving the hook-type fastening members, wherein the backsheet does not extend into the landing zone. The inner layer extends beyond the front transverse edge of the backsheet into the landing zone to form the landing member.

By employing a backsheet which is shorter than the inner layer, the fibrous inner layer is exposed in the front waist region. The fibrous inner layer may be the topsheet which covers the absorbent core, or may be a layer which is located below the absorbent core or which envelops the core.

In a further embodiment of an absorbent article according to the invention, the landing member defines a landing zone for receiving the hook-type fastening members. The backsheet comprises a first section located outside the landing zone and a second section joined to the first section, the second section comprising a different material from the first section. The second section is at least partly located in the front waist region and forms the landing member.

In this way a soft and compliant waist panel is obtained to which no separate patches of loop-type material need be attached. Hence a process simplification is obtained, and no additional bulk is added to the backsheet.

Furthermore, since the landing member is formed by the front waist section of the backsheet, the landing member extends substantially along the full width of the front transverse edge, and hence allows for numerous positions of attachment of the hook-type fastening members. The backsheet section in the front waist region may comprise an elastic non-woven material or may be elasticated and contracted in gathers by a separate elastic element without the landing member interfering with the elastic properties of the front waist region.

In again another embodiment of an absorbent article according to the invention, at least the inner layer on the user-facing side of the article is doubled-over along a fold line in the front waist region such that the inner layer is turned to the garment-facing side of the backsheet and forms the landing member. Attachment means are provided for keeping the inner layer in a doubled-over configuration.

The inner layer may extend beyond the front transverse edge of the backsheet and may be doubled-over onto the backsheet along the front transverse edge. Alternatively, the inner layer is co-extensive with the backsheet, both the backsheet and the inner layer being doubled-over in the front waist region.

By turning the inner layer that is located on the user-facing side of the backsheet, outwardly, a landing member is obtained in a simple manner. No additional loop-type materials, other than those normally used in diaper manufacturing need be attached to form the landing member.

In one embodiment of an article according to the invention, at least two cuts extend through the backsheet extending from the front waist edge in the direction of the back waist edge, wherein the part of the front waist region of the backsheet which extends between the cuts is doubled-over.

By doubling-over the backsheet along these cuts, a low-cut front waist region can be obtained which fits below the belly of the wearer in the so-called "low motion zone". Preferably, a number of cuts extend radially from the front waist edge towards an inwardly concave folding line, such that a number of backsheet-material sections are formed which are each folded along the concave folding line. In this manner a shaped front transverse edge and the landing member are formed simultaneously.

The landing member in the above embodiments is formed by the material of the inner layer, which layer is flexible and can elastically contract and expand to conform to the movements of the wearer. The conformability of the loop-type fastening member according to the invention, to the geometry of the front waist region, is required when elastic elements are located in the front waist region to provide a snug fit of the article around the waist of the wearer.

For fibrous inner layers having relatively little surface irregularities, relatively small and sharply pointed hooks will be required for the hook-type material of the fastening members to be able to engage with such a layer. For non-woven sheets or tissues which comprise a relatively large number of protruding loops at their surface, the hooks of the hook-type material may be of larger size and may be relatively flexible to obtain mechanical attachment to such sheets or tissues. Alternatively, the surface texture of the inner layers can be selected to match a given type of hook-fastening material to achieve proper fastening.

The backsheet may be comprised of a non-woven material, a thermoplastic film or a laminate of a non-woven material and a film. The backsheet may be formed of an elastic material. There may be additional layers located between the topsheet and the backsheet.

BRIEF DESCRIPTION OF THE DRAWINGS

The invention will be described in detail with reference to the accompanying drawings. In the drawings:

FIGS. 16–19 show cross-sectional views of different embodiments of the absorbent article of FIG. 15 along the longitudinal centerline, FIG. 20 shows a schematic perspective view of an absorbent article wherein the backsheet comprises a curved front transverse edge, FIG. 21 shows a cross-sectional view of the absorbent article of FIG. 20 along line 20—20, FIG. 22 shows a cross-sectional view of an alternative embodiment of the absorbent article of FIG. 20 along line 20—20, FIG. 23 shows an enlarged schematic sectional view of a pre-strained landing member comprising a number of parallel corrugations, FIG. 24 shows a schematic perspective view of an absorbent article comprising a landing member as shown in FIG. 23.

DETAILED DESCRIPTION OF THE INVENTION

Mechanical fastening systems of the present invention are useful and beneficial when applied to disposable absorbent articles. As used herein, the term "disposable absorbent article" refers to articles which absorb and contain body exudates and, more specifically, refers to articles which are placed against or in proximity to the body of the wearer to absorb and contain the various exudates discharged from the body and which are intended to be discarded after a single use (i.e., they are not intended to be laundered or otherwise restored or reused). A preferred embodiment of the disposable absorbent article of the present invention is a diaper 20. As used herein, the term "diaper" refers to a garment generally worn by infants or incontinent persons that is drawn up between the legs and fastened about the waist of the wearer. Examples of the kinds of diapers to which the present invention is very readily adapted are shown in the above-referenced U.S. Pat. No. Re. 26,151 issued to Duncan et al. and in U.S. Pat. No. 3,860,003 entitled "Contractable Side Portions for Disposable Diaper" which issued to Kenneth B. Buell on Jan. 14, 1975.

It will be apparent form the following description that the mechanical fastening system illustrated and described herein may be applied to the body portion of such diapers. On the other hand, it will be understood that the invention is not limited to any specific diaper structure or configuration.

Figure 1:
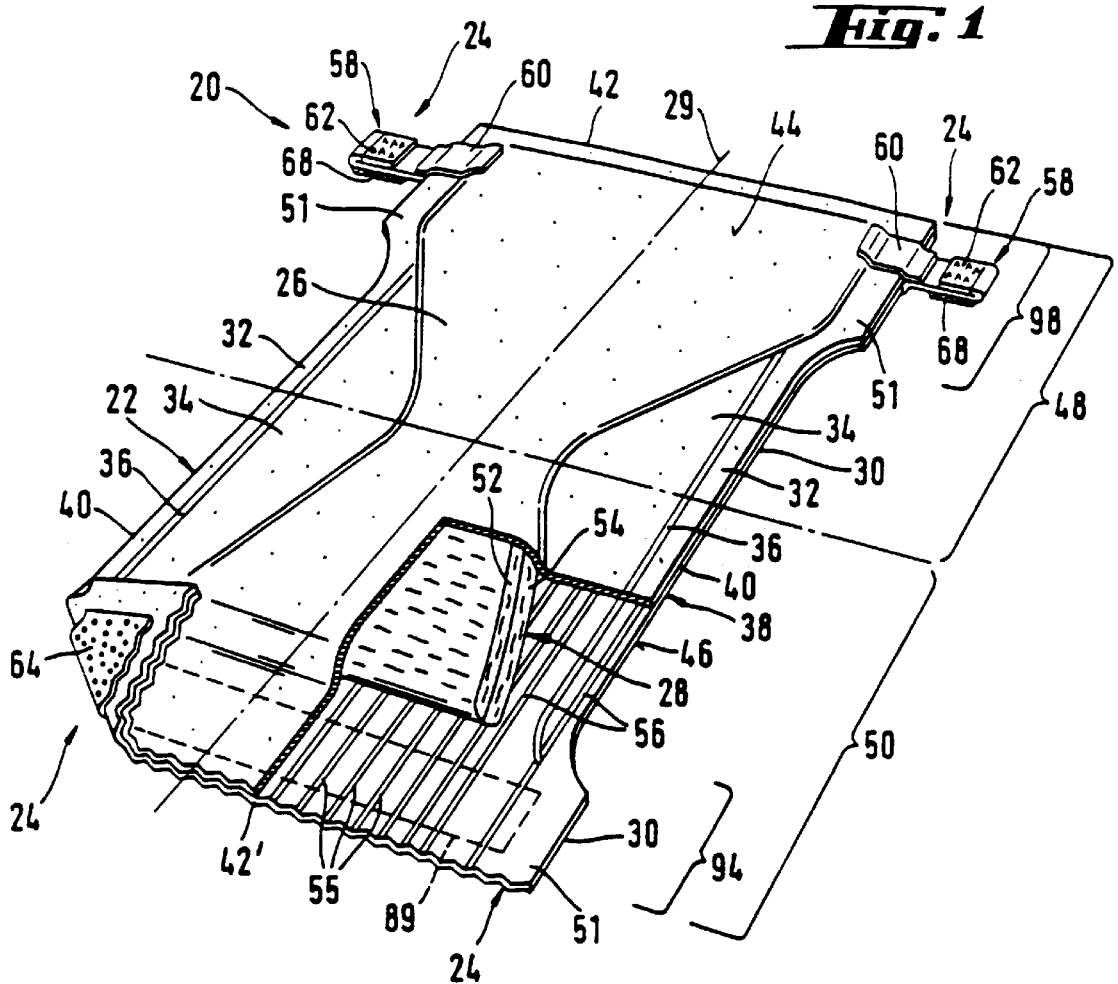
FIG. 1 shows a partially cut-away perspective view of a disposable diaper comprising an elastically extends landing member according to the invention.

Referring to the drawings, it will be noted that FIG. 1 is a partially cut-away perspective view of the diaper 20 of the present invention prior to its being placed on the diaper wearer by the diaper user. As can be seen in FIG. 1, a preferred diaper 20 comprises a body portion 22 and a fastening system 24. A preferred body portion 22 comprises a liquid pervious topsheet 26, an absorbent core 28, a liquid impervious backsheet 30, and elastically contractible leg cuffs 32 comprising a side flap 34 and one or more elastic members 36. While the topsheet 26, the absorbent core 28, the backsheet 30, the side flaps 34, and the elastic members 36 may be assembled in a variety of well-known configurations, a preferred disposable diaper configuration is shown and described generally in the above-referenced U.S. Pat. No. 3,860,003 which issued to Kenneth B. Buell on Jan. 14, 1975.

FIG. 1 shows a preferred embodiment of the body portion 22 in which the topsheet 26 and the backsheet 30 are coextensive and have length and width dimensions generally larger than those of the absorbent core 28. The topsheet 26 is superposed on the backsheet 30 thereby forming the periphery 38 of the body portion 22. The periphery 38 defines the outer perimeter or, in other words, the outer extent of the body portion 22. The periphery 38 comprises longitudinal sides 40 and end edges or transverse edges 42, 42'. The body portion 22 has user-facing side 44 and garment-facing 46. In general, the garment-facing side 46 of the diaper 20 extends from back transverse edge 42 to front transverse edge 42' of the diaper and from one longitudinal side 40 to the other longitudinal side 40 of the diaper and is the surface farthest from the wearer during use of the diaper 20. The garment-facing side of any layer comprised in the diaper 20 is the side of the layer farthest from the wearer during use. When a backsheet 30 is used, it typically forms the garment-facing side 46 of the body portion 22. The user-facing side 44 is that surface of the diaper opposite the garment-facing side 46 and in the embodiment shown is typically formed by the topsheet 26. In general, the user-facing side 44 of the diaper 20 is that surface coextensive with the garment-facing side 46 and which is for the greater part in contact with the wearer when the diaper 20 is worn. The user-facing side of any layer comprised in the diaper 20 is the side of the layer closest to the user when the diaper 20 is worn.

The diaper 20 has first and second end regions 48 and 50, respectively, extending from the transverse edges 42, 42' of the diaper periphery 38 toward the transverse centerline of the diaper 20. Both the first end region 48 and the second end region 50 extend a distance of about one-half of the length of the diaper 20 such that the end regions comprise each half of the diaper 20.

Both the first end region 48 and the second end region 50 have panels 51. The panels 51 are those portions of the first end region 48 and the second end region 50 which overlap when the diaper 20 is fastened about the waist of the wearer. The extent to which the end regions overlap and thus the extent to which the panels 51 are formed will depend on the overall dimensions and shape of the diaper 20 and the size of the wearer.

The absorbent core 28 of the body portion 22 may be any means which is generally compressible, conformable, non-irritating to the wearer's skin, and capable of absorbing and retaining liquids and certain body exudates. The absorbent core 28 may be manufactured in a wide variety of sizes and shapes (e.g., rectangular, hourglass, asymmetric, etc.) and from a wide variety of liquid absorbent materials commonly used in diapers and other disposable absorbent articles, such as comminuted wood pulp which is generally referred to as the airfelt. Examples of other suitable absorbent materials include creped cellulose wadding, absorbent foams, absorbent sponges, superabsorbent polymers, absorbent gelling materials, or any equivalent materials or combination of materials. The total absorbent capacity of the absorbent core 28 should, however, be compatible with the design exudate loading in the intended use of the diaper 20. Further, the size and absorbent capacity of the absorbent core 28 may varied to accommodate wearers ranging from infants to adults.

While the absorbent core 28 may comprise a single layer of absorbent material such as the configuration described in U.S. Pat. No. 4,610,678 entitled "High-Density Absorbent Structure" which issued to Paul T. Weisman and Steven A. Goldman on Sept. 9, 1986 a preferred embodiment of the absorbent core 28 is a dual-layered absorbent core in a preferred configuration such as is generally described in U.S. Pat. No. 4,673,402 entitled "Absorbent Article With Dual-Layered Cores" which issued to Paul T. Weisman, Dawn I. Houghton and Dale A. Gellert on Jun. 16, 1987, having an asymmetric-shaped upper layer 52 and a lower layer 54. The upper layer 52 preferably acts as a liquid acquisition/distribution layer comprised primarily of hydrophilic fiber material. The lower layer 54 acts as a liquid storage layer comprised of a mixture of hydrophilic fiber material and particles of an absorbent gelling material (hydrogel material).

Both the upper layer 52 and the lower layer 54 preferably comprise an absorbent layer encased in a tissue layer. It should be understood, however, that the size, shape, configuration, and total absorbent capacity of the upper layer 52 or the lower layer 54 may be varied to accommodate wearer's ranging from infants through adults. Therefore, the dimensions, shape, and configuration of both the upper layer 52 and the lower layer 54 may be varied (e.g., the upper layer or the lower layer may have a varying caliper, a hydrophilic gradient, a rapid acquisition zone or may contain absorbent gelling material).

The absorbent core 28 is superposed on the backsheet 30 and is preferably associated thereto by a core attachment means 55 such as those well known in the art, for example, pressure-sensitive adhesives, hot melt adhesives or other adhesives; ultrasonic bonding; or heat/pressure sealing. The absorbent core 28 may be secured to the backsheet 30 by a uniform continuous layer of adhesive, a patterned layer of adhesive, or any array of separate lines or spots of adhesive. And adhesive which has been found to be satisfactory is preferably a hot-melt adhesive such as manufactured by Eastman Chemical Products Company of Kingsport, Tenn. and marketed under the tradename of Eastobond A-3 or by Century Adhesives, Inc., of Columbus, Ohio and marketed under the tradename Century 5227. The core attachment means 55 preferably comprise an open pattern network of filaments of adhesive as is shown in U.S. Pat. No. 4,573,986 entitled "Disposable Waste-Containment Garment" which issued to James A. Minetola and David R. Tucker on Mar. 4, 1986.

The backsheet 30 is impervious to liquids and is preferably manufactured from a thin plastic film, although other flexible liquid impervious materials may also be used. The backsheet 30 prevents the exudates absorbed and contained in the absorbent core 28 from soiling articles which contact the diaper 20 such as bedsheets and undergarments. Preferably, the backsheet 30 is a polyethylene film having a thickness of from 0.012 mm (0.5 mil) to 0.051 mm (2.0 mils), although other flexible, liquid impervious materials may be used. As used herein, the term "flexible" refers to materials which are compliant and which will readily conform to the general shape and contours of the human body.

A suitable polyethylene film is manufactured by Monsanto Chemical Corporation and marketed in the trade as Film No. 8020. The backsheet 30 is preferably embossed and/or matte finished to provide a more clothlike appearance. Further, the backsheet 30 may permit vapors to escape from the absorbent core 28 while still preventing exudates from passing through the backsheet 30.

The size of the backsheet 30 is dictated by the size of the absorbent core 28 and the exact diaper design selected. In a preferred embodiment, the backsheet 30 has a modified hourglass shape extending beyond the absorbent core a minimum distance of at least 1.3 cm to 2.5 cm (0.5 to 1.0 inch) around the entire diaper periphery 38.

The topsheet 26 of the body portion 22 of the present invention is compliant, soft feeling, and non-irritating to the wearer's skin. Further, the topsheet 26 is liquid pervious permitting liquids to readily penetrate through its thickness. A suitable topsheet 26 may be manufactured from a wide range of materials such as porous foams, reticulated foams, apertured films, natural fibers (e.g. wood or cotton fibers), synthetic fibers (e.g., polyester or polypropylene fibers) or from a combination of natural and synthetic fibers. Preferably, it is made of a hydrophobic material to isolate the wearer's skin from liquids retained in the absorbent core 28.

A particularly preferred topsheet 26 comprises staple length polypropylene fibers having a denier of about 1.5, such as Hercules Type 151 polypropylene fibers marketed by Hercules, Inc. of Wilmington, Delaware. As used herein, the term "staple length fibers" refer to those fibers, having a length of at least 15.9 mm (0.625 inches).

There are a number of manufacturing techniques which may be used to manufacture the topsheet 26. For example, the topsheet 26 may be woven, non-woven, spunbonded, carded, hydroformed or the like. A preferred topsheet 26 is carded and thermally bonded by means well-known to those skilled in the fabric art. Preferably, the topsheet 26 has a basis weight from 15 to about 30 grams per square meter, a minimum dry tensile strength of at least 400 grams per centimeter in the machine direction and a wet tensile strength of at least 55 grams per centimeter in the cross-machine direction.

The topsheet 26 and the backsheet 30 are associated together in any suitable manner as is well known in the diaper manufacturing art. As used herein, the term "associated" encompasses configurations whereby the topsheet 26 is directly joined to the backsheet 30 by affixing the topsheet 26 directly to the backsheet 30, and configurations whereby the topsheet 26 is indirectly joined to the backsheet 30 by affixing the topsheet 26 to intermediate members which in turn are affixed to the backsheet 30. In a preferred embodiment, the topsheet 26 and the backsheet 30 are joined directly to each other in the diaper periphery 38 by a flap attachment means 56 such as an adhesive or any other attachment means as is known in the art. In general, the core attachment means 55 that affixes the absorbent core 28 to the backsheet 30 is the same means as the flap attachment means 56 that affixes the topsheet 26 to the backsheet 30. Thus, for example, a uniform continuous layer of adhesive, a patterned layer of adhesive, an array of separate lines or spots of adhesive, or a network of adhesive filaments such as shown in the above-referenced U.S. Pat. No. 4,573,986 may be used.

Elastically contractible leg cuffs 32 are disposed adjacent the periphery 38 of the body portion 22, preferably along each longitudinal edge 40, so that the leg cuffs 32 tend to draw and hold the diaper 20 against the legs of the wearer While the leg cuffs 32 may comprise any of several means as are well known in the diaper art, a particularly preferred leg cuff construction comprises a side flap 34 and one or more elastic members 36, as is described in detail in the hereinbefore referenced U.S. Pat. No. 3,860,003. In addition, a method and apparatus suitable for manufacturing a disposable diaper having elastically contractible leg cuffs are described in U.S. Pat. No. 4,081,301 entitled "Method and Apparatus For Continuously Attaching Discrete, Stretched Elastic Strands to Predetermined Isolated Portions of Disposable Absorbent Articles" which issued to Kenneth B. Buell on Mar. 28, 1978.

In a preferred embodiment, the elastically contractible leg cuff 32 comprises a side flap 34 and an elastic member 36 comprising an elastic thread.

The diaper 20 comprises a front waist elastic element 89, which in FIG. 1 is formed by the elastic landing member 64. The front waist elastic element 89 preferably extends between 5% and 60% at a force of between 30 and 280 g per inch, preferably about 30% at a force of 150 g per inch and contracts the front waist region 94 in gathers to provide an elasticated fit of the waist region 94 against the waist of a wearer.

Generally, the front waist elastic element 89 may be located on the garment-facing side or on the user-facing side of the topsheet 26 and the backsheet 30, or may be comprised between the topsheet and the backsheet.

The diaper 20 is provided with a fastening system 24 for forming a side closure. By applying the hook-type fastening members 58 to the loop-type landing member 64, the diaper 20 is fitted to the wearer and the first end region 48 and the second end region 50 are maintained in an overlapping configuration when the diaper 20 is worn.

In a preferred embodiment of the present invention as shown in FIG. 1, the fastening system 24 comprises a fastening member 58, preferably comprising a tape tab 60 and a hook-type fastening element 62, disposed adjacent each longitudinal side 40 of the body portion 22 in the back waist region 98 of the first end region 48; a landing member 64, engageable with the hook-type fastening element 62, disposed on the outside surface 46 of the body portion 22 in the front waist region 94. Additional fastening/disposal means 68 may be positioned on the tape tab 60, for allowing the diaper 20 to be secured in a disposal configuration so as to provide convenient disposal of the diaper 20.

Each fastening member 58 is intended to provide a mechanical fastening means for engaging the landing member 64 so as to provide a secure side closure for the diaper 20.

The fastening member 58 may comprise a combination of a hook-type fastening element and adhesive attachment means positioned on the body portion 22 of the diaper 20. The hook-type fastening element 62 of each fastening member 58 is joined to the body portion and preferably covers an area 25 mm wide (i.e., generally perpendicular to the longitudinal centerline 29) by 62.5 mm long (i.e., generally parallel to the longitudinal centerline 29) at the panels 51 of the body portion 22. An exemplary embodiment of a hook-type fastening member 62 is described in U.S. Pat. No. 4,699,622 entitled "Disposable Diaper Having an Improved Side Closure" issued to John W. Toussant and Margaret H. Hasse on Oct. 13, 1987.

Figure 2:
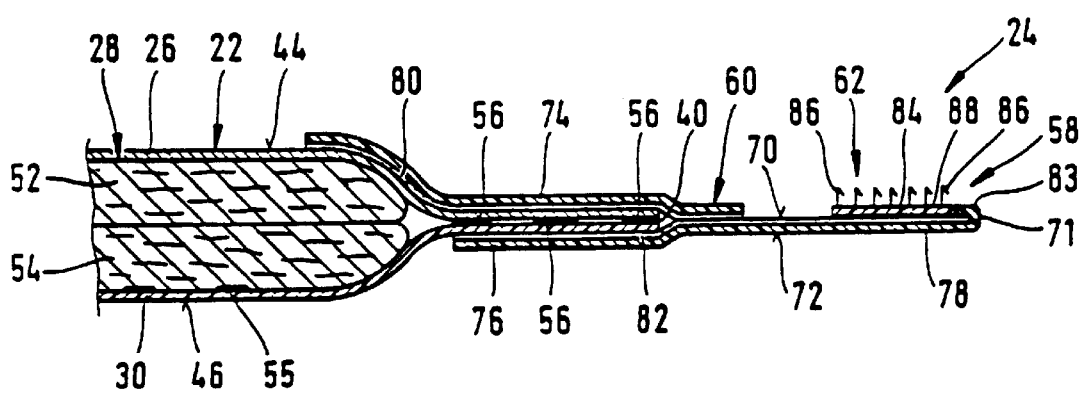
FIG. 2 shows a cross-sectional view through a hook-type fastening member of FIG. 1 along a line of cross section parallel to the back transverse edge.

As shown in FIGS. 1 and 2, the fastening member 58 most preferably comprises a tape tab 60. Any of the well known configurations and constructions of a tape tab may be used. A preferred tape tab 60 is a Y-shaped tape tab as described in detail in GB-A-1458566. Alternatively preferred tape tabs are described in detail in co-pending European Patent Application No. 87300450.1.

A particularly preferred tape tab 60 is illustrated in FIG. 2 and has a fastening surface 70 and a backing surface 72. The fastening surface 70 is that surface of the tape tab 60 designed to engage the landing member 64 of the present invention. Thus, the fastening surface 70 of the tape tab 60 will generally correspond to the garment-facing side 44 of the body portion 22. The backing surface 72 is that surface opposite of the fastening surface 70 and generally corresponds to the outside surface 46 of the body portion 22. The backing surface 72 is thus generally exposed during wear of the diaper 20.

The preferred tape tab 60 illustrated in FIG. 2 is one which is anchored to both the user-facing side 44 and the garment-facing side 46 of the body portion 22 to create a manufacturer's end (i.e., that attachment of the tape tab 60 to the diaper 20 made during manufacture of the diaper 20). The tape tab 60 has another element which forms the user's end i.e., that joint made by the person in securing the diaper to the wearer). Thus, the preferred tape tab 60 of the present invention has at least three elements, a first fixed portion 74, a second fixed portion 76, and a connective portion 78. The first fixed portion 74 is that portion of the tape tab 60 which is attached to the user-facing side 44 of the body portion 22. The second fixed portion 76 is that portion of the tape tab 60 which is attached to the garment-facing side 46 of the body portion 22. The first fixed portion 74 and the second fixed portion 76 thus form the manufacturer's end of the tape tab 60. The connective portion 78 is that portion of the tape tab 60 which is attached to another portion of the diaper 20, generally the landing member 64 by the user when securing the diaper 20 on the wearer. The connective portion 78 thus forms the user's end. Additionally, the outer surface of the second fixed portion 76 and the outer surface of the connective portion 78 form the backing surface 72 of the tape tab 60 while the inner surface of the first fixed portion 74 and the inner surface of the connective portion 78 form the fastening surface 70 of the tape tab 60.

The preferred Y-shaped tape tab 60 of the present invention can be constructed in several ways. The first fixed portion 74, the second fixed portion 76, and the connective portion 78 can each be separate tapes which meet and are joined adjacent the longitudinal edge 40 of the body portion 22 in an area of joinder. A more practical structure for the tape tab 60 is one in which the connective portion 78 and either the first fixed portion 74 or the second fixed portion 76 are a unitary strip of tape material. If the connective portion 78 is unitary with the second fixed portion 76 as shown in FIG. 2, then the first fixed portion 74 is a separate element which is attached to the combined connective portion and the second fixed portion adjacent to the longitudinal side 40 of the body portion 22.

FIG. 2 also shows tab attachment means for securing the tape tab 60 to the body portion 22. These tab attachment means are any of those attachment means which provide an adequate bond, and preferably are any of the pressure-sensitive adhesives well-known to those of ordinary skill in the adhesive art. The outer surface of the first fixed portion 74 is affixed to the user-facing side 44 of the body portion 22 by a first tab attachment means 80. The inner surface of the second fixed portion 76 is affixed to the garment-facing side 46 of the body portion 22 by a second tab attachment means 82. The connective portion is provided with a first fastening element 62 joined to it preferably by the second tab attachment means 82 (alternatively, a third tab attachment means if the connective portion 78 is a separate element from the second fixed portion 76), although an adhesive attachment means may be placed on the first fastening element 62 separately and the combined material joined to the connective portion 78.

Preferred materials for the tape tabs 60 comprises a tape material such as tape code numbers XPF 14.43.0, Y-9376, or Y-9030 available from The Minnesota Mining and Manufacturing Company, St. Paul, Minn. The tape material in the embodiments are preferably a polyethylene film having a tab attachment means tailored to bond to the polyethylene positioned on the tape material. The tape tab attachment means may comprise any of those adhesives which provide an adequate bond with other portions of the diaper, and is preferably any of the pressure-sensitive adhesives well-known to those of ordinary skill in the art. Preferred tab attachment means is a pressure-sensitive adhesive such as code number XPF 1.42.34 available from The Minnesota Mining an Manufacturing Company, St. Paul, Minn.

As shown in FIG. 2, the tape tab 60 may also have a grip tab 83 at the distal edge 71 in the connective portion 78. The grip tab 83 may be formed by folding over a small margin of the distal edge 71 of the connective portion 78 and attaching it to itself. This forms an end on the connective portion 78 which is easier to grasp by the diaper user when the diaper 20 is to be fitted and attached to the wearer. The grip tab 83 is most beneficial when used when the connective portion 78 is superposed on the first fixed portion 74.

The hook-type fastening element 62 of the present invention comprises a hook fastening material 84. As used herein, the term "hook fastening material" is used to designate a material having engaging elements 86. It should also be understood that the use of the term "hook" should be non-limiting in the sense that the engaging elements 86 may comprise any shapes as are known in the art so long as they are adapted to engage a complementary second fastening element 66. As shown, the hook fastening material 84 preferably comprises a base 88 having a first surface and a second surface and a plurality of engaging elements 86 extending from the first surface of the base 88. Each of the engaging elements 86 are shown to comprise a stem supported at one end on the first surface of the base and an enlarged head positioned at the end of the stem opposite of the base.

The hook fastening material 84 of the present invention is intended to engage fibrous elements of fibrous material on the user-facing side 44 of the backsheet, which fibrous material may for instance be formed by the topsheet 26 or by a waist shield 91. Thus, the hook fastening material 84 may be manufactured from a wide range of materials. Suitable materials include nylon, polyester, polypropylene, or any combination of these materials. A suitable hook fastening material 84 comprises a number of shaped engaging elements 86 projecting from a woven backing such as the commercially available material designated "Scotchmate" brand No. FJ3402 available from Minnesota Mining and Manufacturing Company, St. Paul, Minn. Alternatively, the engaging elements may have any shape such as hooks, "T's" or any other shape as are well known in the art. A particularly preferred hook fastening material is described in C. Locke Scripps' co-pending U.S. patent application Ser. No. 07/007,841 entitled "Disposable Diaper Having An Improved Fastening Device" filed Jan. 26, 1987.

Other suitable hook-type materials for use in the present invention are for instance extruded hooks available under the reference MC5 from the Minnesota Mining and Manufacturing Company, ST. Paul, Minn. or printed hooks available from the same company under references CS200 and MC6. Other suitable hook-type materials are available under reference 942 or 960E from Aplix, Inc., P.O. Box 7505, Charlotte, N.C. 28241.

The landing member 64 comprises a loop-type material such as for instance the fibrous topsheet material.

As used herein, the term "loop-type" material is intended to mean any fibrous material which can mechanically engage with the hook-type material of the fastening members 58 to maintain the diaper 20 affixed around the waist of a wearer, or in a disposal configuration. A suitable loop-type material is described in U.S. Pat. No. 5,326,612 (Goulait).

Other suitable loop-type materials for use in the present invention may comprise woven materials such as brushed loops available from Texmaille S.A, Rue Pasteur, 02610 Moy de L'aisne, France; double knit loops available from Tissages de Quintenas S.A., Parc d'activites de marenton, B.P.158-07104 Annonay, France; and Linerless loops available under reference LLL from the Minnesota Mining and Manufacturing Company.

Again other suitable loop-type materials are formed by non-woven materials.

In general, the materials of the hook-type fastening members 58 and the loop-type landing member 64 should be selected such that the peel force of a 30 mm wide patch of hook-type material is between 3 and 20 N, preferably about 7-8 N and the shear force of a patch of hook-type material of dimensions of 30×13 mm is between 10 and 100 N, preferably about 50 N.

The tests for measuring the peel forces and the shear forces exerted by the hook-type fastening members 58 on the loop type landing member 64 are described below.

I. 135°-Peelforce Test

This method describes the procedure for measuring the peel force, in grams, of the combined hook-type fastening member and loop-type landing member. The materials under test are mounted on a steel plate-sled assembly and are separated at a constant peel angle of 135°.

During the test the temperature is maintained at 73±2° F. The relative humidity is controlled at 50±2%.

A patch of loop-type material measuring 2 in.×4 in. is placed on a 2 in.×8 in.×0.06 in. steel plate with a double-sided tape of the same dimensions as the patch of loop-type material.

A patch of hook-type material measuring 1 in.×0.75 in. is attached to a tape tab of similar kind as the tape tab 60 shown in FIG. 1, adjacent the area of the grip tab 83, further referred to in this test method as the leading edge of the tape tab 60. No actual grip tab needs be present at the leading edge of the tape tab 60 during testing. If the hooks of the hook-type material are angled with respect to the tape tab, the hooks are oriented to be inclined towards the leading edge.

The hook-type material is placed on the loop-type landing member. Subsequently, a rubber-coated steel roller of diameter of 3.25 in., a width of 1.75 in. and a weight of 4.5 lbs is rolled back and forth in the length direction of the tape tab 60 twice (a total of four passes).

The steel plate with the attached hook-type and loop-type materials is mounted into an INSTRON test apparatus, Model 4201, which is set to have a cross-head speed of 12 in./minute and a Load Cell of 1 kg.

The steel plate is slidably mounted in a sled which is carried by the lower jaw of the INSTRON apparatus.

The leading edge of the tape tab 60 is placed in the upper jaw of the INSTRON apparatus.

The upper cross head is set in motion to pull the leading edge of the tape tab 60 off the loop-type landing member at an angle of 135° with respect to the loop-type landing member. The steel test plate on which the loop-type landing member is mounted, is moved in the sled consecutively with the cross head relative to the lower jaw to maintain a constant angle of 135° during the full cycle of peeling off the tape tab.

The peak force, in grams, is recorded for at least four samples and is averaged.

II. 180° Shear Test

This method describes the procedure for measuring the shear force, in grams, of the combined hook-type fastening member and loop-type landing member. The materials under test are mounted on a steel plate and are separated at a constant peel-angle of 180°.

During the test the temperature is maintained at 73±2° F. The relative humidity is controlled at 50±2%.

A patch of loop-type material measuring 2 in.×5 in. is placed on a 2 in.×5 in.×0.06 in. steel plate with a double-sided tape of the same dimensions as the patch of loop-type material.

A patch of hook-type material measuring 1 in.×0.75 in. is attached to a tape tab of similar kind as the tape tab 60 shown in FIG. 1, adjacent the area of the grip tab 83, further referred to in this test method as the leading edge of the tape tab 60. No actual grip tab needs be present at the leading edge of the tape tab 60 during testing. If the hooks of the hook-type material are angled with respect to the tape tab, the hooks are oriented to be inclined away from the leading edge.

The hook-type material is placed on the loop-type landing member. Subsequently, a rubber-coated steel roller of diameter of 3.25 in., a width of 1.75 in. and a weight of 4.5 lbs is rolled back and forth in the length direction of the tape tab 60 twice (a total of four passes).

The steel plate with the attached hook-type and loop-type materials is mounted horizontally into the lower jaw of an INSTRON test apparatus, Model 4201, which is set to have a cross-head speed of 12 in./minute, a Load Cell of 10.0 kg and a gage length of 2 in.

The leading edge of the tape tab 60 is placed in the upper jaw of the INSTRON apparatus.

The upper cross head is set in motion to pull the leading edge of the tape tab 60 off the loop-type landing member at an angle of 1850 with respect to the loop-type landing member. When the maximum pull force has been reached, the crosshead is returned to the pre-set gage length.

The peak force, in grams, is recorded for at least four samples and is averaged.

FIGS. 3 to 7 show cross-sectional views of different embodiments of the front waist region 94 of the diaper of FIG. 1 along a line or cross-section parallel to the front transverse edge 42' and running through the front waist elastic member 89. In FIGS. 3–6, the front waist section 94 is shown in its flattened state, i.e. the elastic elements 89 in the front waist region 94 are stretched.

Figure 3:
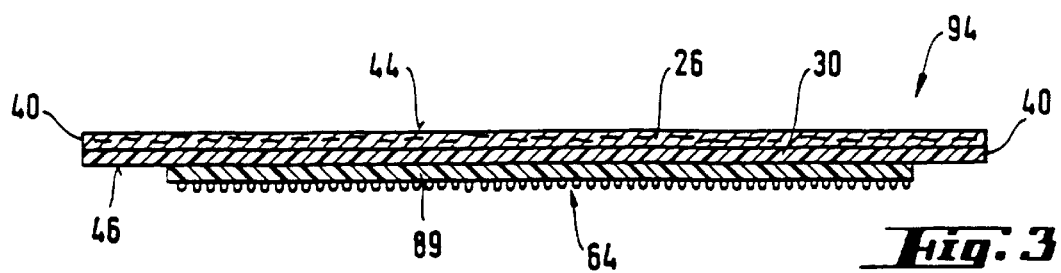
FIGS. 3–7 show a cross-sectional view of different embodiments of the front waist region of the diaper of FIG. 1 along a line of cross-section parallel to the front transverse edge and running through the front waist elastic element.

In the embodiment of FIG. 3, the landing member 64 is made of an elastic loop-type material, which may be an elastic non-woven material or which may be a loop-type material comprising elastic strands or elastic fibers. The landing member 64 is located on the garment-facing side 46 of the backsheet 30 and forms the front waist elastic element 89.

Figure 4:
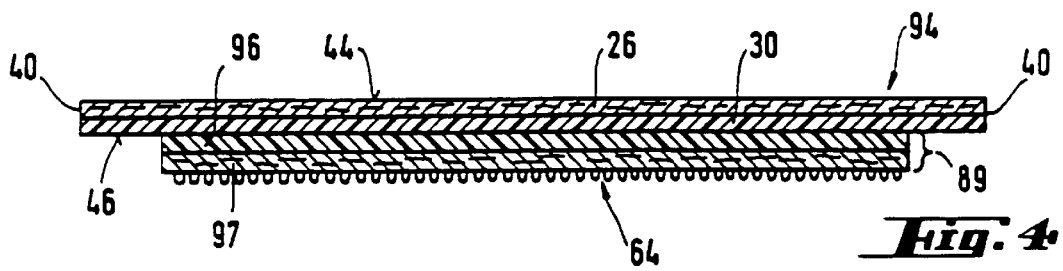

FIG. 4 shows an embodiment wherein the landing member 64 comprises a laminate of an elastomeric film 96 and a loop-type material 97. The loop-type material 97 is bonded to the film 96 for instance by adhesive bonding or by ultrasonic bonding. A suitable film is available from EXXON as type no. 500 a suitable loop-type material is available from Amoco as fabric type no. P8. The laminate 96,97 may be formed by attaching the loop-type material 97 to the elastomeric film 96 while the film is in a pre-stretched state, such that the loop-type material is contracted by the film 96 to form gathers. Alternatively, the laminate 96,97 may be formed by attaching the loop-type material 97 to the film 96 while the film is in its relaxed state. Such a laminate material may be activated, to impart extensibility thereto prior to attaching it to the topsheet or the backsheet, or after attaching it to the topsheet or backsheet, by mechanically deforming the fibrous layer 97 by drawing it, or by passing it through a pair of corrugated rolls. By such a treatment, a number of fibers of the layer 97 will break or will become disentangled, so that this layer becomes extensible in the direction of the front transverse edge 42'. Mechanically activating a so-called "zero strain" elastic laminate has been described in European patent application no. 93117656.4 and in U.S. Pat. No. 5,196,000 and U.S. Pat. No. 5,236,430.

Another type of elastic laminate comprises a fibrous layer 97 attached to a film 96, which film is heated such that it elastically contracts to form an elastic laminate.

Figure 5:
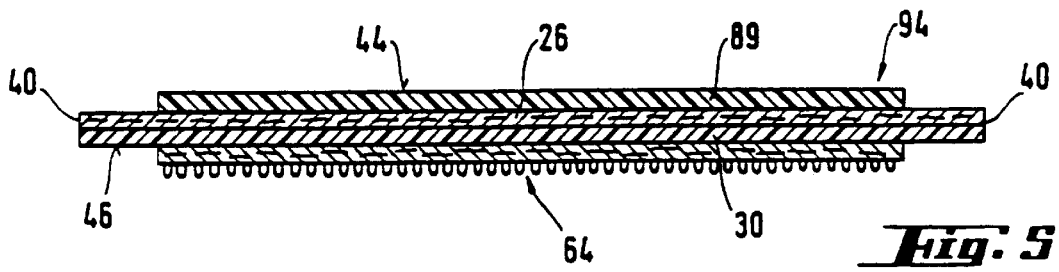

In the embodiment of FIG. 5, the front waist elastic element 89 is connected to the user-facing side 44 of the topsheet 26. The landing member 64 is connected to the garment-facing side 46 of the backsheet 30, and is contracted by the elastic element to form transverse gathers, which run generally perpendicular to the front transverse edge 42'. The landing member 64 is in itself non-elastic, but is elastically extensible by at least 5%, preferably by at least 30%.

Figure 6:
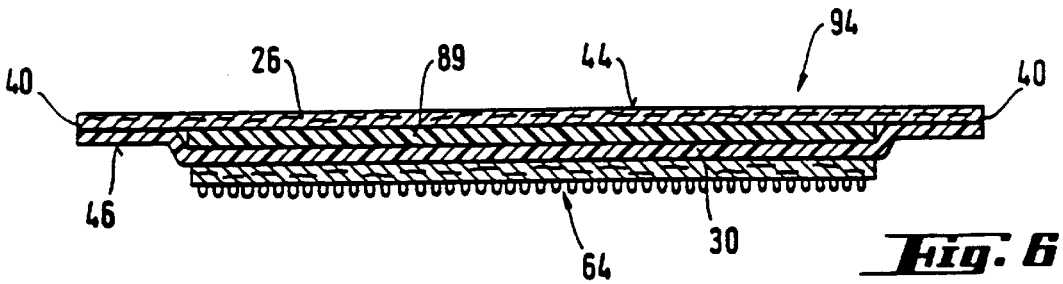

In the embodiment of FIG. 6, the elastic element 89 is sandwiched between the topsheet 26 and the backsheet 30. The landing member 64 is located on the garment-facing side 46 of the backsheet 30.

Figure 7:
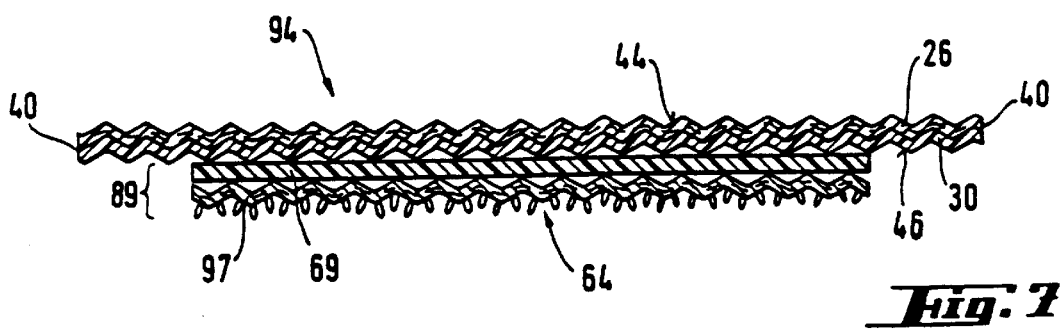

In the embodiment of FIG. 7, the elastic element 96 is shown in its relaxed state, the backsheet 30 and the landing member 64 being gathered by the contracted elastic element 96. Instead of the gathers in the topsheet 26 and the backsheet 30 being caused by contraction of the elastic element 96, the corrugations as shown in FIG. 7 may also have been imparted by passing the backsheet 30, the loop-type material 97 and the elastic film 96 through a pair of intermeshing grooved rolls while the elastic film 96 is in its relaxed state, as described in U.S. Pat. No. 5,236,430.

Figure 8:
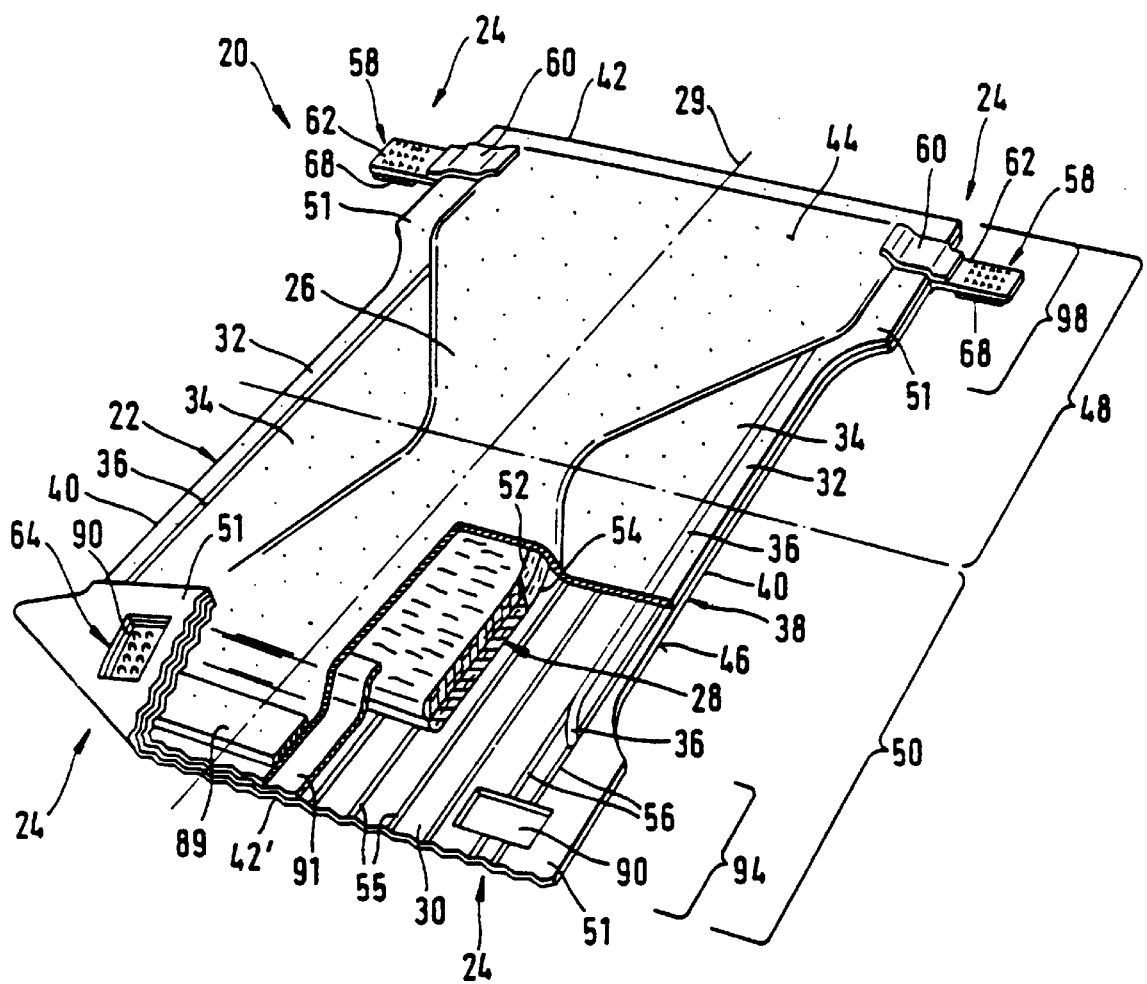
FIG. 8 shows a partially cut-away perspective view of a disposable diaper comprising an elastically extensible landing member comprising cut-out sections in the backsheet.

FIG. 8 shows an embodiment wherein the backsheet 30 comprises cut-out sections 90 in the front waist region 94. The topsheet 26 is exposed at the garment-facing side 46 of the backsheet 30 in the region of the cut-out sections 90 to form the landing member 64. The elastic element 89 contracts the topsheet in transverse gathers, which will cause the fibers of the topsheet 26 to stand away from the topsheet surface and which will cause parts of the topsheet 26 to project outwardly from the cut-out sections 90. This will improve the fastening of the hook-type fastening member 58 to the landing member 64.

Figure 9:
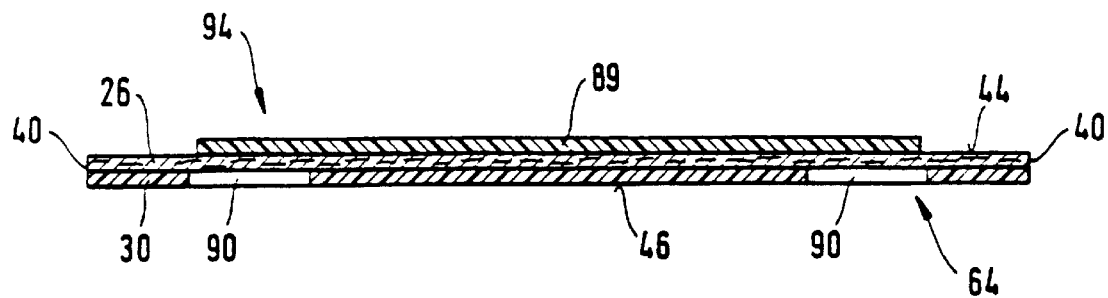
FIGS. 9–11 show cross-sectional views of different embodiments of the front waist region of the diaper of FIG. 8 along a line or cross-section parallel to the front transverse edge and running through the front waist elastic element.
Figure 10:
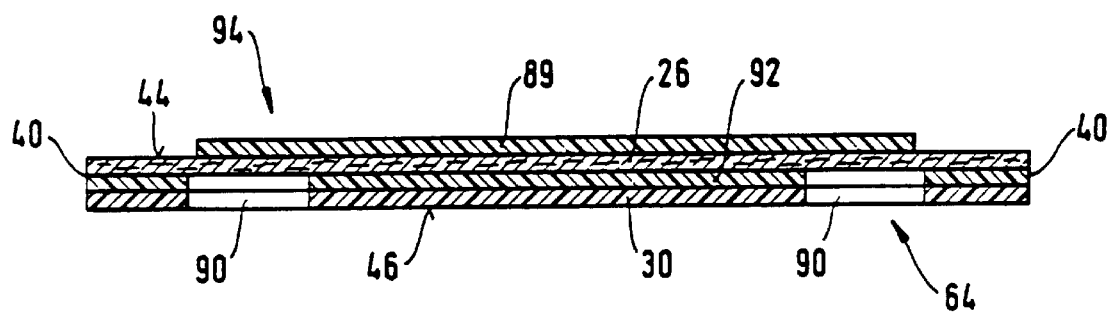

FIG. 9 shows a cross-sectional view of the front waist region 94 of the diaper of FIG. 8 along a line or cross-section parallel to the front transverse edge 42' and running through the front waist elastic member 89. The cut-out sections, or holes, 90 through the backsheet 30 expose the topsheet 26 which forms an inner layer on the user-facing side 44 of the backsheet 30 which can engage with the hooks of the fastening member 58. In the embodiment of FIG. 10, and additional layer 92 is located between the topsheet 26 and the backsheet 30. The layer 92 may for instance be a polyethylene film, located between the topsheet and the core 28 along the front transverse edge of the core to prevent leakage therefrom, the layer 92 being in this case a so-called "waist shield". Alternatively, the layer 92 may be a tissue underlying the core and being co-extensive with the backsheet 30. In again another embodiment, the inner layer 92 is co-extensive with the backsheet 30 and is laminated to the user-facing side 44 of the backsheet 30, and may comprise a thermoplastic film. In this case the backsheet 30 is preferably formed by a non-woven layer, which provides a soft and cloth-like garment-facing surface 46. In case the inner layer 92 is unsuitable for becoming mechanically attached to the hook-type fastening members 58, the cut-out sections 90 extend through the inner layer 92 up to the inner layer which is adapted to entangle with, and to attach to the hook-type fastening members 58.

Figure 11:
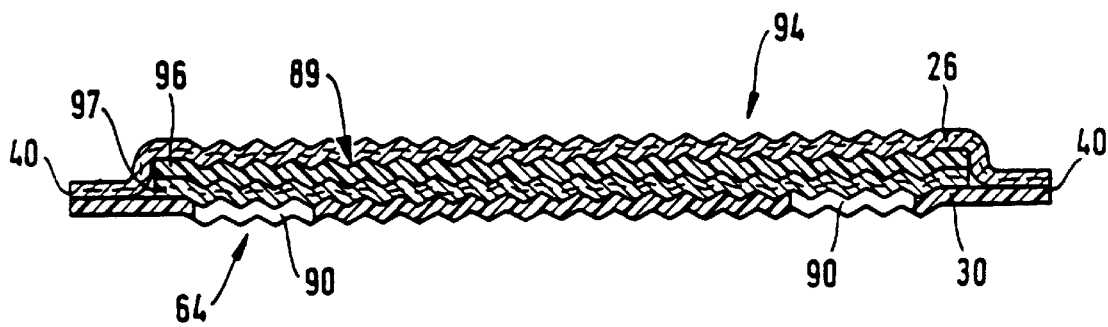

FIG. 11 shows a cross-sectional view of the front waist region 94 along a line of cross section parallel to the front transverse edge 42', wherein an elastic laminate 96,97 is comprised along the front waist edge 42' between the topsheet 26 and the backsheet 30. The laminate comprises a nonwoven layer 97 and an elastomeric film 96 attached to the nonwoven layer 97. The elastic laminate contracts the front waist edge 42' in a number of gathers such that the fibers of the layer 97 project outwardly into the apertures 90.

Figure 12:
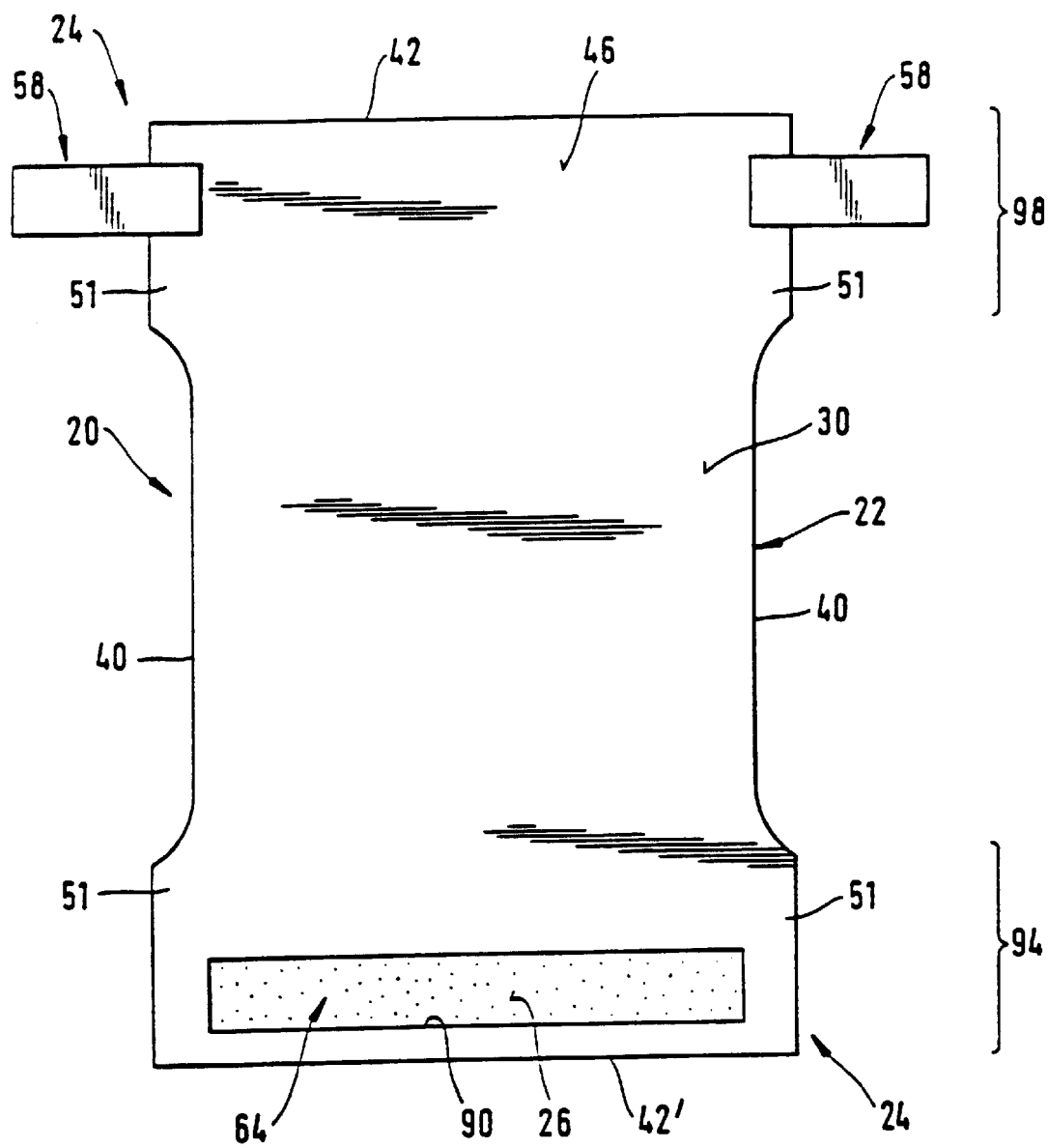
FIGS. 12–14 show schematic perspective views of the garment-facing side of different embodiments of an absorbent article comprising cut-out sections in the backsheet.
Figure 13:
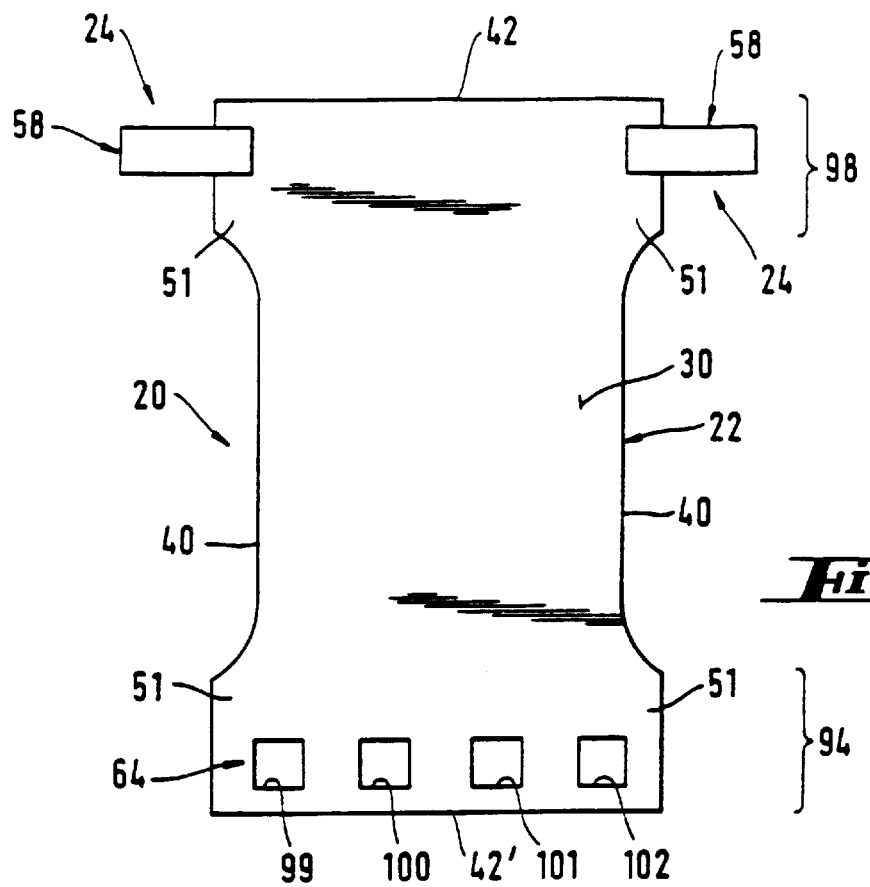

FIG. 12 schematically shows a plan view of the garment-facing side of an absorbent article 20 wherein the landing member 64 is comprised of a single strip-shaped aperture in the backsheet 30 alongside the front transverse edge 42'. In the embodiment of FIG. 13, the landing member 64 comprises a number of individual cut out regions 99,100,101 and 102 located in the front waist region 94.

Figure 14:
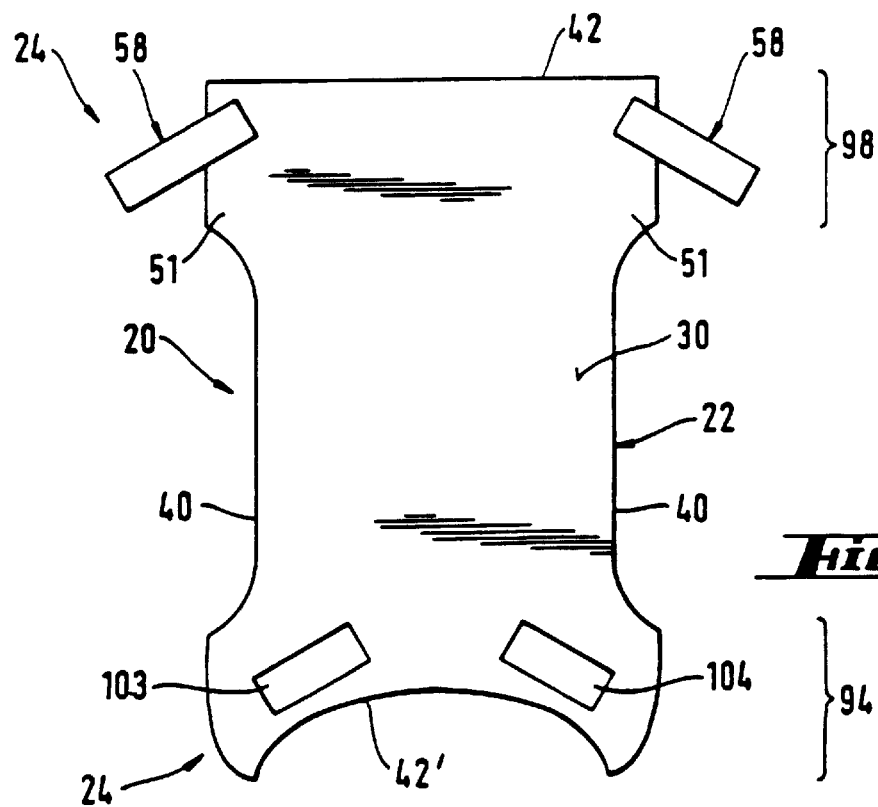

FIG. 14 shows an embodiment wherein the front transverse edge 42' of the backsheet 30 is curved. The cut-out sections 103, 104 are placed at an angle with respect to that front transversed edge 42' to receive the angled fastening members 58. An absorbent article of this shape fits well below the belly of the wearer and will be located in the low-motion zone of the wearer. Hence the front waist region 94 will be subject to little movement and will stay properly in place.

The fastening members 58 may comprise a loop-type material 68 on their backing surface 72, as shown in FIG. 1. This has as an advantage that the closure members 58 can be used to mutually engage for keeping the diaper 20 in a rolled-up disposal configuration as described in EP-A- 321 234.

Figure 15:
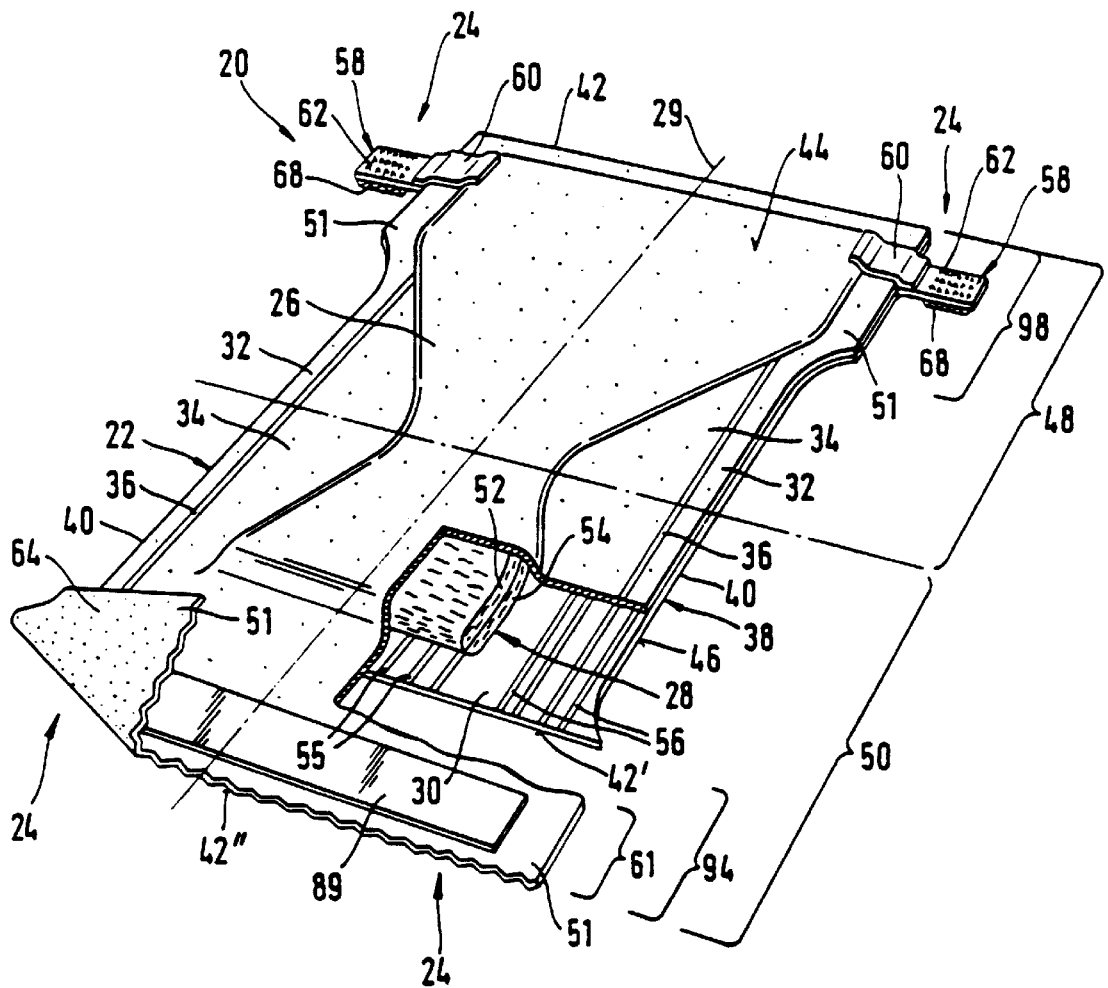
FIG. 15 shows a partially cut-away perspective view of a disposable diaper wherein the topsheet projects beyond the backsheet in the front waist region.

In the embodiment of FIG. 15, the backsheet 30 comprises a front transverse edge 42' which is located below the topsheet 26 inboard from the front transverse edge 42" of the topsheet 26. The backsheet 30 does not extend into the landing zone 61, which is defined by the garment-facing surface to which the hook-type fastening members 58 can attach when the article 20 is placed on a wearer. The topsheet 26 extends beyond the front transverse edge 42' of the backsheet and forms the landing member 64. The front waist elastic element 89 is connected to the user-facing side 44 of topsheet 26.

FIG. 16 shows a cross-sectional view of the absorbent article of FIG. 15 along the longitudinal center line 29. The elastic element 89 is located on the garment-facing side 46 of the topsheet 26, and is for instance formed by a laminate of an elastomeric film 96 and a fibrous layer 97 to which the hook-type fasteners may engage. In this case the underlying topsheet material may be comprised of an apertured plastic film or of a fibrous material which is in itself unsuitable for attachment to the hook-type fastening members 58.

In FIG. 17 it is depicted that the elastic member 89 is located on the user-facing side 44 of the topsheet 26, as is also shown in FIG. 1. FIG. 18 depicts an embodiment wherein an inner layer 91 forms a waist shield against leakage of exudates from the front transverse edge 59 of the core 28. The inner layer 91 projects beyond the front transverse edge 59 of the core 28 and beyond the front transverse edge 42' of the backsheet 30 and forms the fastening member 64. In the embodiment of FIG. 19, the elastic element 89 is comprised between an inner layer 91, which is co-extensive, but not coterminous with the backsheet 30 and the topsheet 26. The inner layer 91 in this case may be a core-reinforcement layer or may be a non-woven inner layer, laminated to the backsheet 30. The elastic element is comprised between the inner layer 91 and the topsheet 26.

FIG. 20 shows an embodiment wherein the backsheet 30 comprises a curved front transverse edge 42' which defines the contour of a waist panel. The inner layer 91, which is uncovered by the backsheet 30 in the front waist region 94, forms the landing member 64. The inner layer 91 extends between edge 93 and front edge 42". In FIGS. 21 and 22, a cross-sectional view along the line 20—20 of FIG. 20 is shown. The inner layer 91 may be made of an elastic material and may be flat, i.e. without gathers, as shown in FIG. 21. In this case the front waist elastic element 89 is formed by the elastic layer 91.

Alternatively, the inner layer 91 is in itself non-elastic, but is contracted along a number of transverse gathers by a separate front waist elastic element 89, as shown in FIG. 22. The transverse gathers causes the fibers of the inner layer 91 to stand-up and project outwardly and thereby increase the fastening capacity of the hook-type material thereto. The transverse gathers may be formed by elastic contraction of the elastic material 87. Alternatively, the transverse gathers may be obtained by mechanical pre-straining of the inner layer to form parallel corrugations. In case the pre-straining imparts a degree of elasticity to an originally non-elastic web, the front waist elastic member 89 may be omitted, the pre-strained inner layer 91 forming the waist elastication.

FIG. 23 shows a partial enlarged plan view of a pre-strained inner layer 91 in the front waist region 94. The inner layer 91 comprises a number of parallel corrugations 120, 121. In case the inner layer 91 is not elastically extensible, these corrugations 121,122 impart a degree of elastic extensibility of between 0–50%, preferably between 10% and 20% to the layer 91. Additionally, the mechanical treatment of the inner layer 91 by which the fibers of the inner layer become disentangled to a larger or smaller degree in the process of forming the corrugations 120,121, will tend to improve the surface texture of the inner layer 91 for improved fastening of the hook-type material thereto. The process for imparting such surface structure has been described in detail in U.S. Pat. No. 5,196,000 and U.S. Pat. No. 5,236,430 and U.S. application Ser. No. 08/155406, filed on Nov. 19, 1993 in the name of The Procter & Gamble Company.

FIG. 24 shows an embodiment wherein the inner layer 91 comprises a number of parallel corrugations 120,121 and forms an elasticated waist panel in the front waist region. In one embodiment, the layer 91 in FIG. 24 is a laminate of a non-elastic non-woven layer such as the polypropylene fibrous topsheet material and a non-elastic thermoplastic film, such as the polyethylene backsheet film.

Figure 25:
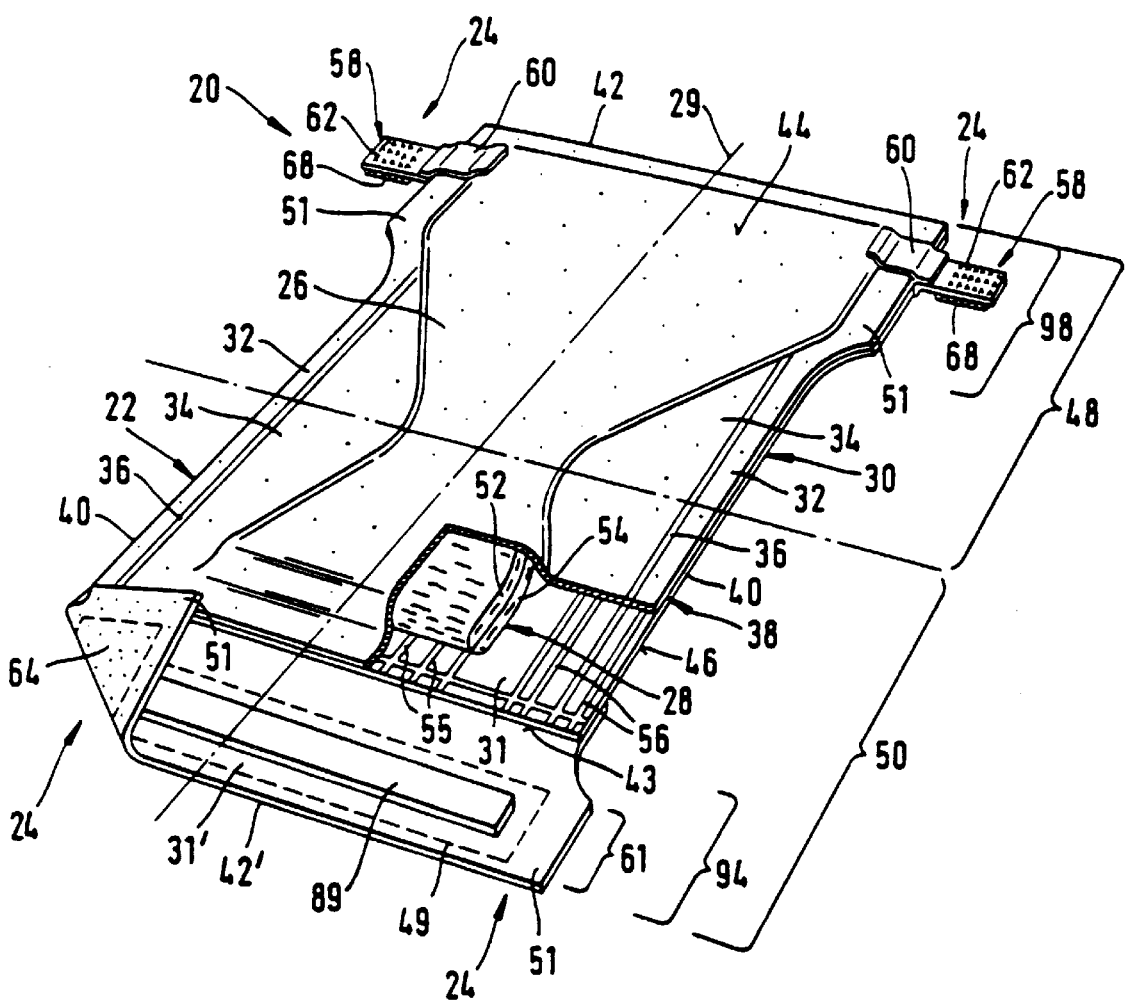
FIG. 25 shows a partially cut-away perspective view of a disposable diaper comprising two different backsheet sections.

In the embodiment of FIG. 25, the backsheet 30 comprises a first backsheet section 31 and a second backsheet section 31'. The first and second sections are mutually attached in the region of a front peripheral edge 43 of the first backsheet section 31. The front backsheet section 31' extends into the landing zone 61, which is indicated in FIG. 25 by dashed line 49. The front backsheet section 31' comprises a loop-type material for engaging with the hook-type fasteners 58. The front backsheet section 31' may be comprised of an elastic non-woven material or may comprise an extensible, non-elastic material which is gathered by a front waist elastic element 89.

Figure 26:
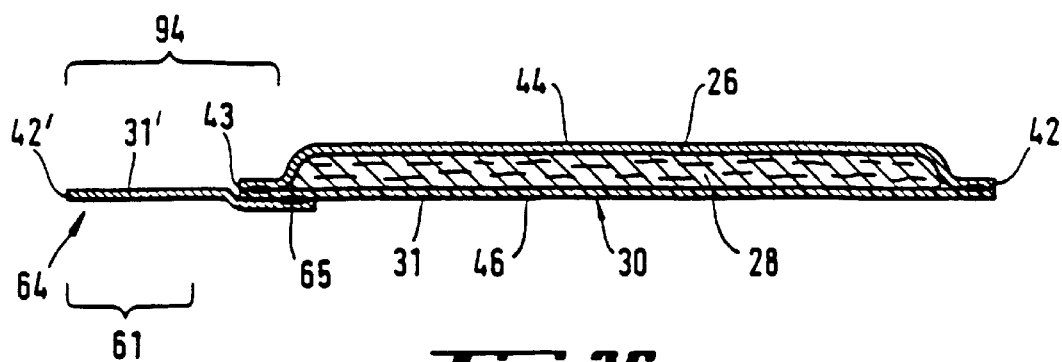
FIGS. 26–28 show cross-sectional views of different embodiments of the absorbent article of FIG. 25 along the longitudinal centerline.
Figure 27:
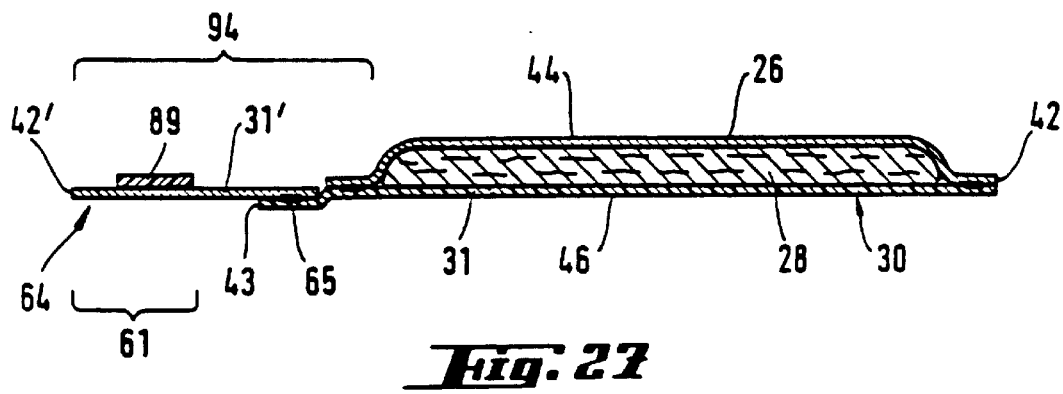
Figure 28:
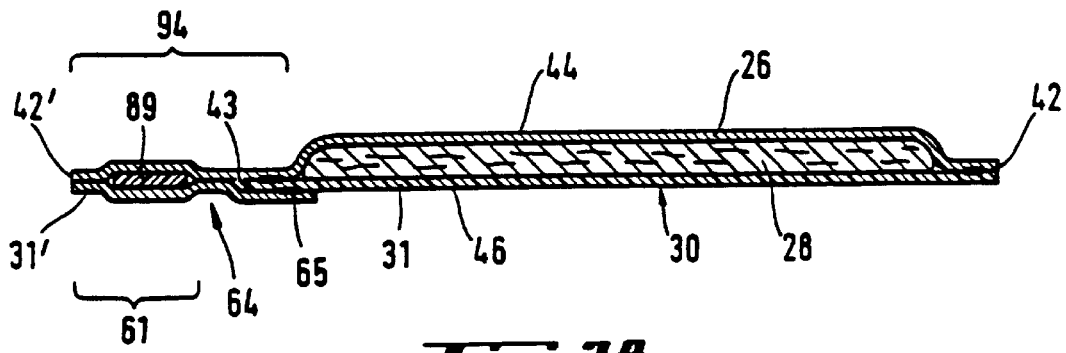

FIGS. 26–28 show cross-sectional views of different embodiments of the absorbent article of FIG. 25, along the longitudinal centerline 29. The front backsheet section 31' is attached to the backsheet section 31 with attachment means 65, which may be adhesive, ultrasonic or heat-seal attachment means. The backsheet section 31 terminates at front peripheral edge 43, which is located outboard from the landing zone 61. The front backsheet section 31' is attached to the garment-facing side 46 of the backsheet section 31. In the embodiment of FIG. 26, the backsheet section 31 underlies the absorbent core 28 and is made of a liquid-impervious thermoplastic film, the front backsheet section 31' being made of a breathable elastic non-woven material.

In the embodiment of FIG. 27, a front waist elastic element 89 is located on the user-facing side 44 of the second section 31' of the backsheet 30. The first backsheet section 31 extends beyond the perimeter of the absorbent core 28, the second backsheet section 31' being connected to the user-facing side 44 of the first section 31.

In the embodiment of FIG. 28, the topsheet 26 extends across the front backsheet section 31. An elastic element 89 is encased between the topsheet 26 and the front backsheet section 31'.

Figure 29:
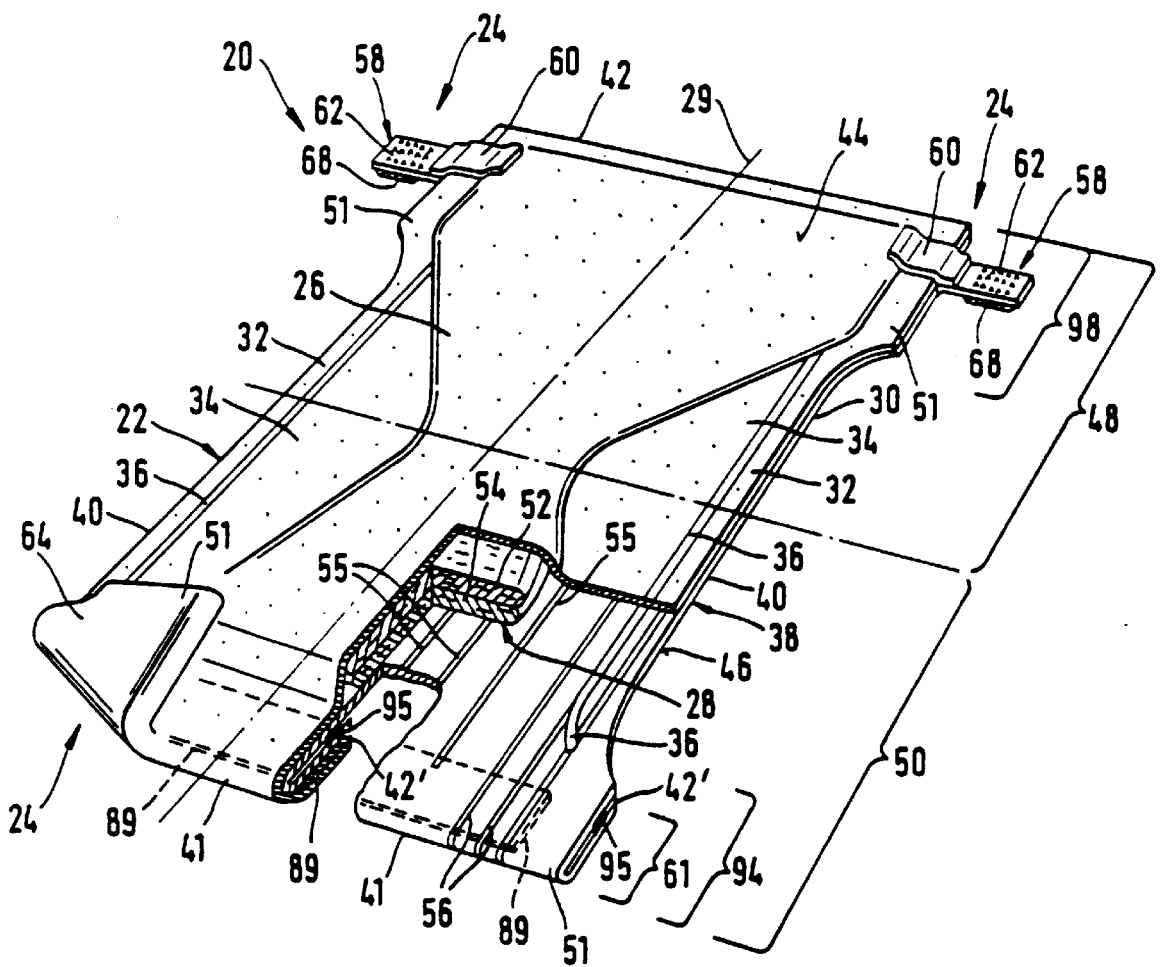
FIG. 29 shows a partially cut-away perspective view of a disposable diaper comprising a doubled-over front waist region.

FIG. 29 shows an embodiment wherein the landing member 64 comprises the topsheet 26, the backsheet 30 and the waist elastic element 89 comprised between the topsheet and the backsheet. The topsheet 26, and the backsheet 30 are folded around fold line 41. The doubled-over combination of the topsheet 26, backsheet 30 and elastic member 89, forms an elastically extensible landing member 64. The front transverse edge 42' of the backsheet 30 is maintained in a folded-over configuration by the fastening means 95, which may be formed by one or more glue beads, and which attach the doubled-over front waist region 94 to the garment facing side 46 of the backsheet 30.

Figure 30:
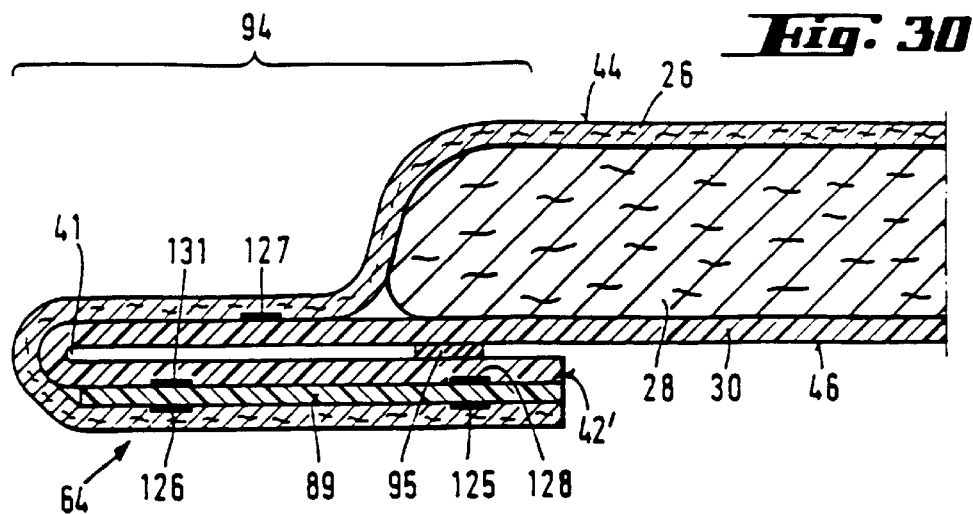
FIGS. 30–32 show schematic cross-sectional views of the front waist region of an absorbent article of FIG. 29, FIGS. 33–36 show schematic perspective views of different embodiments of an absorbent article having a doubled-over front waist region, and FIG. 37 show a disposable absorbent article comprising curved sections of the longitudinal sides in the back waist region, a doubled over front waist region and additional hook-type fasteners attached thereto.

In the embodiment of FIG. 30, the waist elastic element 89 is located between the topsheet 26 and the backsheet 30, and is folded in its entirety around the fold line 41. The topsheet 26, backsheet 30 and waist elastic element 87 are mutually attached by spiral adhesive patterns 125,126,127, 128 and 131.

Figure 31:
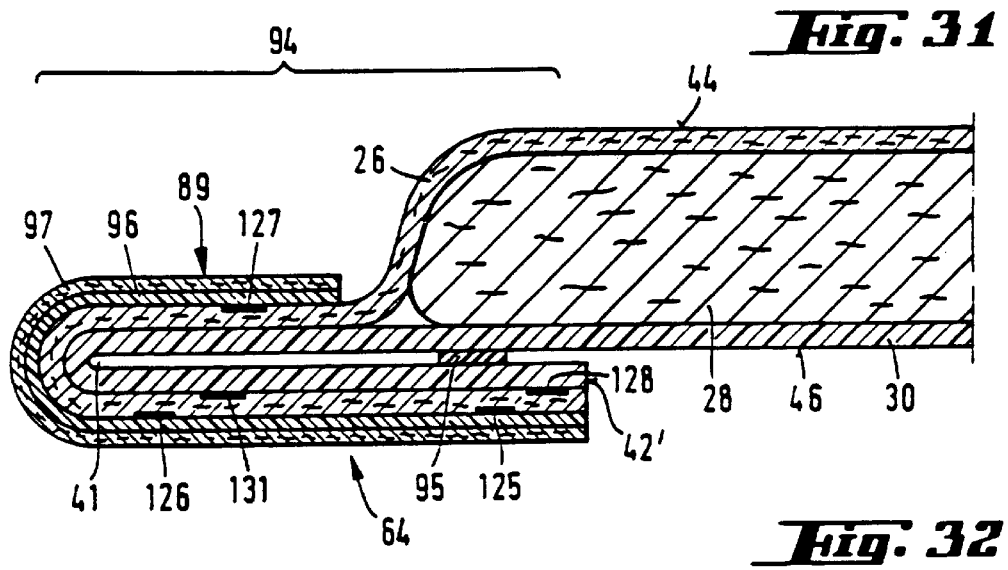

In the embodiment of FIG. 31, the elastic element 89 is located on the user-facing side 44 of the topsheet 26. The elastic element 89 may in this case be comprised of a stretchable non-woven material, which is adapted to engage with the hook-type fastening members. Alternatively, the elastic element 89 comprises a laminate of an elastomeric film 96 and a non-woven layer 97 attached to the elastomeric film. The elastomeric film 96 of the elastic laminate is attached to the topsheet 26, the non-woven layer 97 of the elastic laminate being placed on the user-facing side 44 of the topsheet before folding around the fold line 41. When the front waist section 94 is doubled-over around fold line 41, the non-woven layer 97 of the elastic laminate will be located on the garment-facing side of the backsheet facing outwardly and forming the landing member 64.

Figure 32:
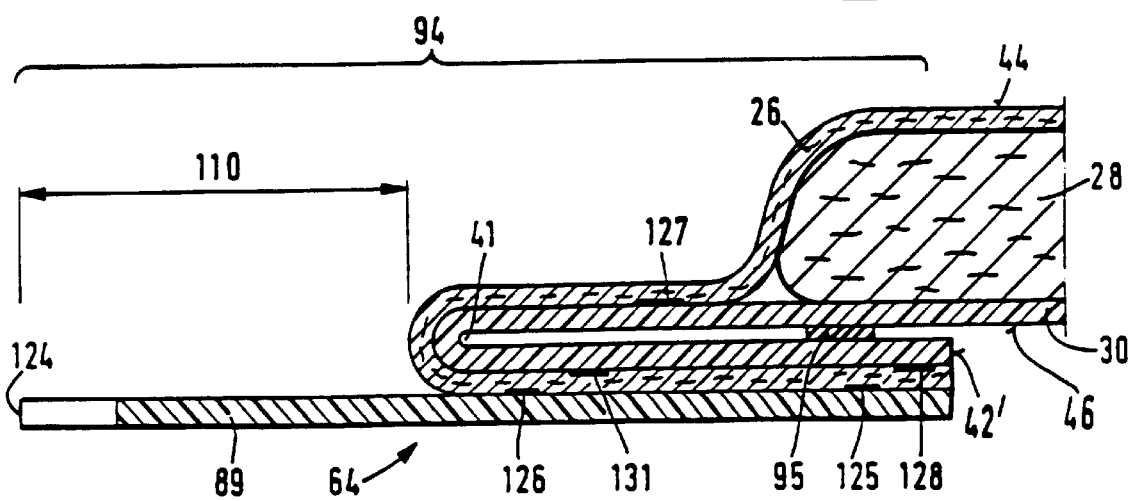

In the embodiment of FIG. 32, the elastic element 89 comprises a region 110 which is unattached to the underlying topsheet layer 26. Upon doubling-over of the topsheet 26 and the backsheet 30 along the fold line 41 in the front waist region 94, the unattached segment 110 of the elastic element 87 protrodes outwardly and forms a flexible and elastic waist panel, which will contact the stomach of the wearer during use.

The inner layer which after doubling-over of the front waist region 94 forms the landing member 64 may alternatively be formed by a layer which underlies the core, similar to layer 91 as shown in FIG. 19, and which is co-extensive with the user-facing side 44 of the backsheet 30. Such an inner layer 91 may be a core-reinforcement layer or may be the lower layer of an envelope layer which enwraps the core 28.

Figure 36:
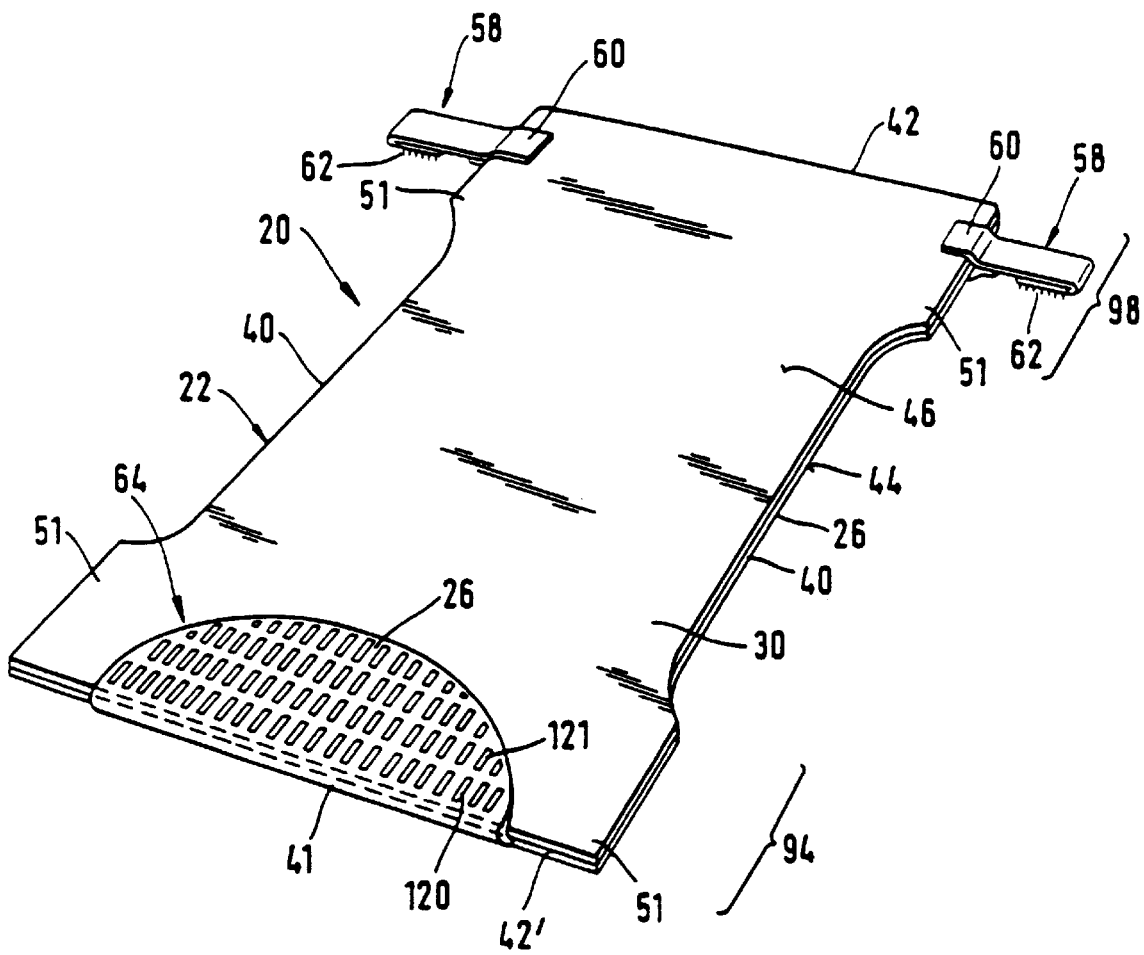

Alternatively, the topsheet 26 may extend beyond the front transverse edge 42' of the backsheet, and may be doubled over along the front transverse edge 42' to form the landing member, as shown in FIG. 36.

Figure 33:
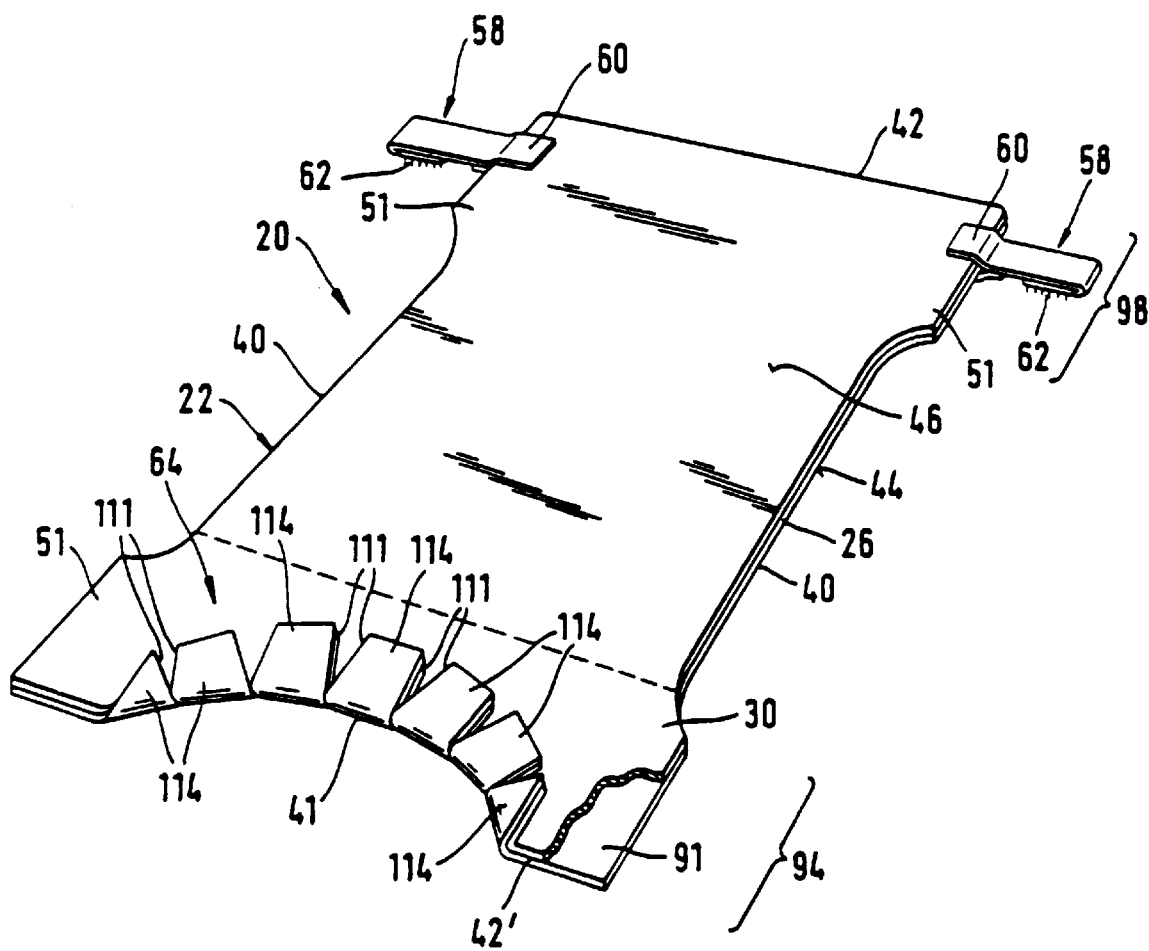

In the embodiment of FIG. 33, a number of cuts 111,112, 113 extend through the backsheet 30 and the inner layer on the user facing side 44 of the backsheet 30 from the front transverse edge 42' towards a fold line 41. A number of sections 114,115,116 and 117 are formed between each pair of neighbouring cuts. The backsheet 30 and inner layer of each section are folded along the fold line 41 to obtain a low-cut front waist region. The fold line 41 in FIG. 33 forms an inwardly concave cut in the front waist region 94. Such a curved front waist section fits well in the low motion zone below the belly of a wearer.

Figure 34:
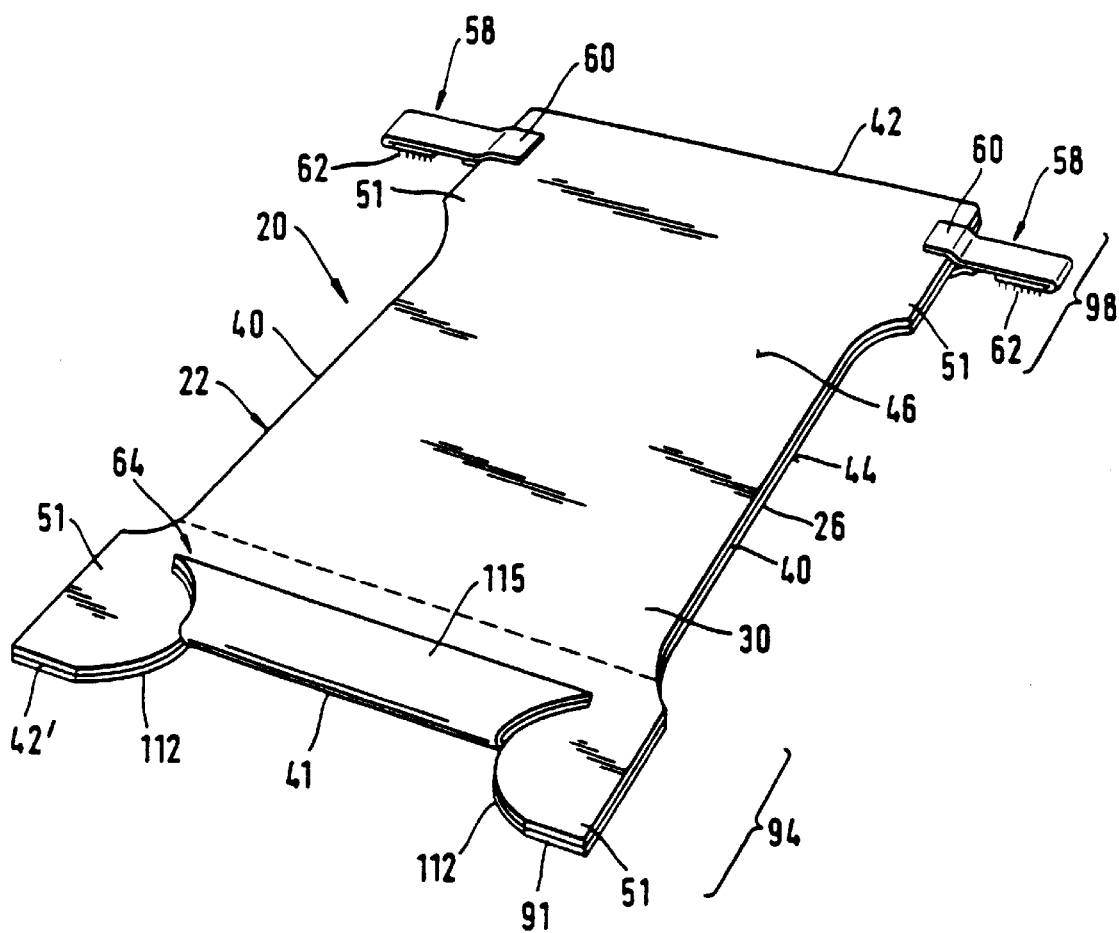

In the embodiment of FIG. 34, only two cuts 112 are provided in the backsheet 30 and the inner layer material such that a single flap is obtained in the front waist region, which is folded over along fold line 41. The folded over sections 114,115 and 117 and the folded-over flap in FIG. 34 may comprise any of the material of the inner layer 91, in case the inner layer 91 extends beyond the front transverse edge 42' of the backsheet 30.

Figure 35:
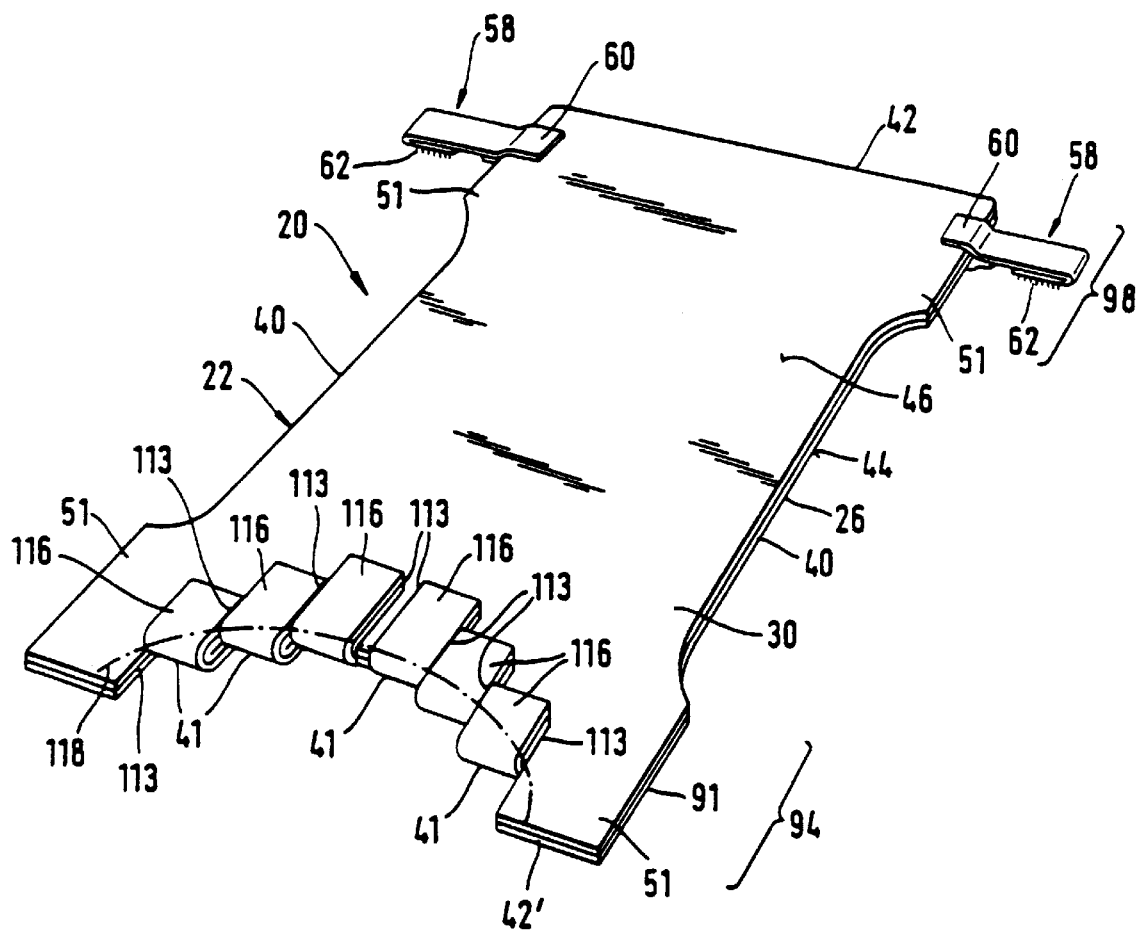

In the embodiment of FIG. 35, the cuts 111,112,113 extend perpendicularly to the front transverse edge 42' of the backsheet 30. Each cut 111,112,113 ends at a fold line 41 which is parallel to the front transverse edge 42'. The doubled over sections 114,115,116 form a stepped waist section, which may be cut along a contour 115 to obtain an inwardly concave waist section.

In the embodiment of FIG. 36, the topsheet 26 extends beyond the front transverse edge 42' of the backsheet 30, the front transverse edge 42' forming the fold line 41. The topsheet 26 and the backsheet 30 in the front waist region 94 are provided with a number of corrugations 120,121, as shown in FIG. 23. No additional elastic elements are applied in the front waist region 94, elasticity being provided by the corrugated topsheet and backsheet layers of the landing member 64.

Figure 37:
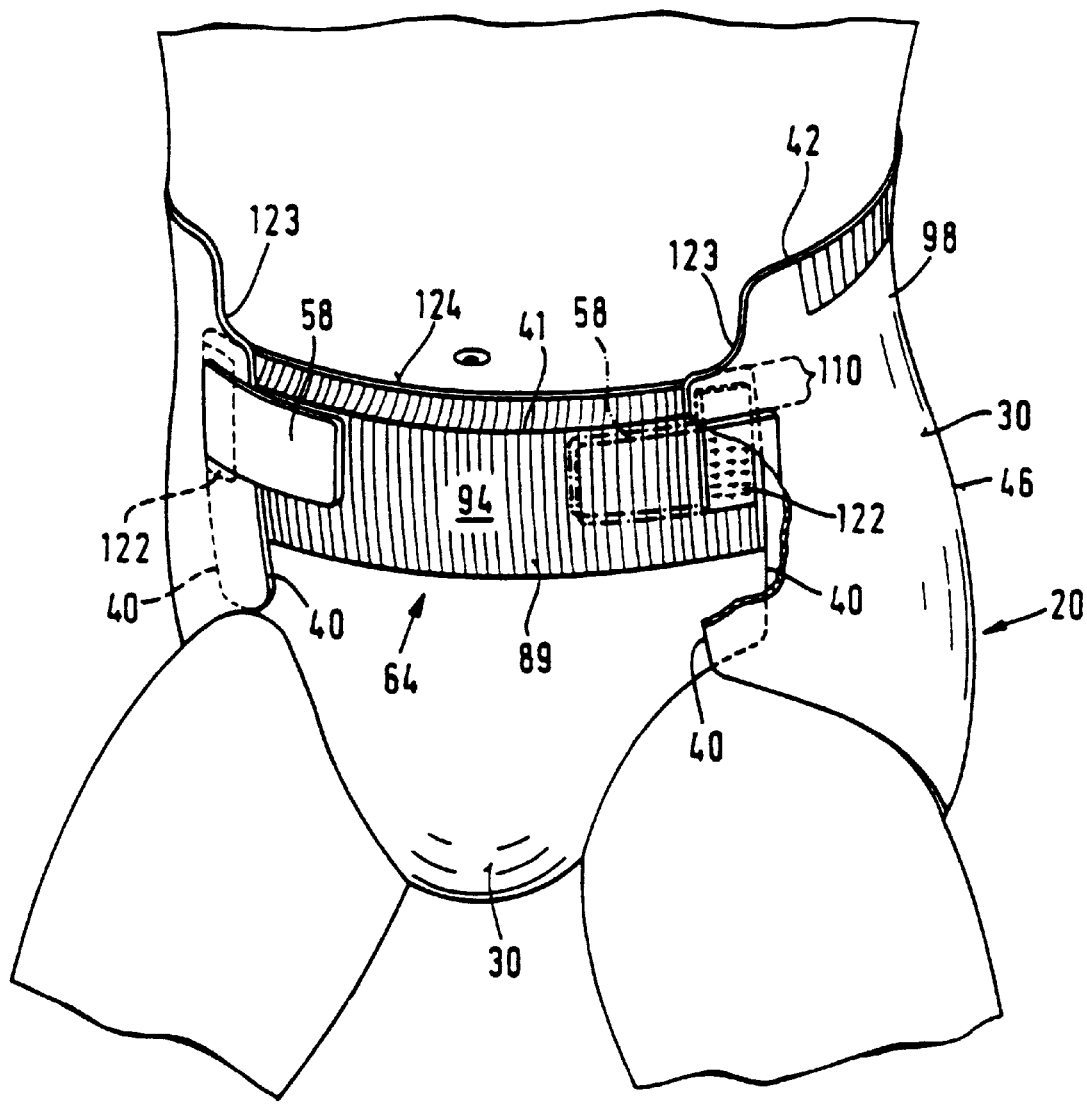

FIG. 37 shows the absorbent article 20 having a landing member as shown in FIG. 32 when put on a wearer. The article 20 comprises rounded sections 123 of the longitudinal sides 40. The rounded sections 123 match with the upper edge 126 of the elastic element 89 and form a rounded contour. Additional patches of hook-type material 122 are located on the doubled-over landing member 64 to connect to the user-facing side (topsheet material) in the back waist region 98. The presence of the additional hook-type material 122 helps to maintain the front and back end regions 48,50 in a properly overlapping relationship on the wearer.

I claim:

1. An absorbent article comprising:
    a backsheet having a user-facing side, a garment-facing side, two longitudinal sides, a first transverse edge, a first waist region located along the first transverse edge, a second transverse edge, and a second waist region located along the second transverse edge,
    an inner layer covering at least a part of the user-facing side of the backsheet,
    an absorbent core located adjacent the user facing side of the backsheet, and
    a mechanical fastening system comprising:
        at least one hook-type fastening member located in the second waist region and extending transversely beyond one longitudinal side, and
        an extensible landing member located in the first waist region for mechanically engaging with the hook-type fastening member, the landing member being formed from an extension of the inner layer which extends beyond the front transverse edge of the backsheet.

2. The absorbent article of claim 1 wherein the landing member is extensible by at least 5%.

3. The absorbent article of claim 1 wherein the landing member is extensible by at least 15%.

4. The absorbent article of claim 1 wherein the landing member is extensible in the direction of the front transverse edge.

5. The absorbent article of claim 1 wherein the landing member comprising an elastic loop-type material which is elastically extensible between 5% and 60% at a force of between 30 and 280 grams per inch.

6. The absorbent article of claim 1 wherein the inner layer comprises a laminate of a first layer of loop-type material and a second, elastomeric layer laminated to the first layer of loop-type material.

7. The absorbent article of claim 1, wherein the length of the landing member is at least one third of the length of the first transverse edge.

8. The absorbent article of claim 1 further including a first waist elastic element located in the first waist region.

9. The absorbent article of claim 8 wherein the landing member is contracted by the waist elastic element.

10. The absorbent article of claim 8 wherein the first waist elastic element includes a pre-stretched member.

11. The absorbent article of claim 1 wherein the landing member is elastically extensible.

12. The absorbent article of claim 1 wherein the inner layer is doubled over the garment-facing side of the backsheet.

13. The absorbent article of claim 12 further including attachment means for keeping the inner layer in a doubled-over configuration.

* * * * *

UNITED STATES PATENT AND TRADEMARK OFFICE
CERTIFICATE OF CORRECTION

| | |
|---|---|
| PATENT NO. | : 5,968,031 |
| DATED | : October 19, 1999 |
| INVENTOR(S) | : Christoph Johann Schmitz |

Page 1 of 1

It is certified that error appears in the above-identified patent and that said Letters Patent is hereby corrected as shown below:

<u>Column 13,</u>
Line 20, "1850" should read -- 185° --.

<u>Column 16,</u>
Line 36, "lamninate" should read -- laminate --.

Signed and Sealed this

Twenty-fifth Day of December, 2001

Attest:

JAMES E. ROGAN
Director of the United States Patent and Trademark Office

Attesting Officer